US011872035B2

(12) United States Patent
Wu et al.

(10) Patent No.: US 11,872,035 B2
(45) Date of Patent: Jan. 16, 2024

(54) CONTINUOUS ANALYTE MONITORING SENSOR CALIBRATION AND MEASUREMENTS BY A CONNECTION FUNCTION

(71) Applicant: Ascensia Diabetes Care Holdings AG, Basel (CH)

(72) Inventors: Huan-Ping Wu, Granger, IN (US); Mark D. Cerutti, Everett, MA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 159 days.

(21) Appl. No.: 17/394,290

(22) Filed: Aug. 4, 2021

(65) Prior Publication Data

US 2022/0039702 A1 Feb. 10, 2022

Related U.S. Application Data

(60) Provisional application No. 63/061,135, filed on Aug. 4, 2020, provisional application No. 63/061,167, filed (Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0002* (2013.01); *A61B 5/1451* (2013.01);
(Continued)

(58) Field of Classification Search
CPC .............. A61B 5/14532; A61B 5/6801; A61B 2560/0223; A61B 5/0002; A61B 5/1451;
(Continued)

(56) References Cited

U.S. PATENT DOCUMENTS

2005/0161346 A1 7/2005 Simpson et al.
2005/0245799 A1 11/2005 Brauker et al.
(Continued)

FOREIGN PATENT DOCUMENTS

WO WO2018104835 A1 6/2018
WO WO2020161099 A1 8/2020

OTHER PUBLICATIONS

U.S. Appl. No. 17/394,279, filed Aug. 4, 2021, Wu et al.
(Continued)

*Primary Examiner* — Nathan J Jenness
*Assistant Examiner* — Meghan R Kumar
(74) *Attorney, Agent, or Firm* — Erise IP, P.A.

(57) ABSTRACT

A method of determining glucose values during continuous glucose monitoring (CGM) measurements includes providing a CGM device including a sensor, a memory, and a processor; applying a constant voltage potential to the sensor; measuring a primary current signal resulting from the constant voltage potential and storing the measured primary current signal in the memory; applying a probing potential modulation sequence to the sensor; measuring probing potential modulation current signals resulting from the probing potential modulation sequence and storing measured probing potential modulation current signals in the memory; determining an initial glucose concentration based on a conversion function value and the primary current signal; determining a connection function based on the primary current signal and a plurality of the probing potential modulation current signals; and determining a final glucose concentration based on the initial glucose concentration and the connection function value. Other aspects are provided.

21 Claims, 16 Drawing Sheets

Related U.S. Application Data on Aug. 4, 2020, provisional application No. 63/061,157, filed on Aug. 4, 2020, provisional application No. 63/061,152, filed on Aug. 4, 2020.

(51) Int. Cl.

| | |
|---|---|
| *G16H 40/67* | (2018.01) |
| *A61B 5/1486* | (2006.01) |
| *G01N 33/487* | (2006.01) |
| *G01N 33/49* | (2006.01) |
| *G16H 50/30* | (2018.01) |
| *G16H 50/70* | (2018.01) |
| *G16H 40/40* | (2018.01) |
| *A61B 5/1495* | (2006.01) |

(52) U.S. Cl.
CPC .......... *A61B 5/1486* (2013.01); *A61B 5/6801* (2013.01); *A61B 5/72* (2013.01); *A61B 5/7228* (2013.01); *G01N 33/48707* (2013.01); *G01N 33/49* (2013.01); *G16H 40/67* (2018.01); *A61B 5/1495* (2013.01); *A61B 5/14865* (2013.01); *A61B 2560/0223* (2013.01); *G16H 40/40* (2018.01); *G16H 50/30* (2018.01); *G16H 50/70* (2018.01)

(58) Field of Classification Search
CPC ....... A61B 5/1486; A61B 5/72; A61B 5/7228; A61B 5/14865; A61B 5/1495; G01N 33/48707; G01N 33/49; G16H 40/67; G16H 40/40; G16H 50/30; G16H 50/70
See application file for complete search history.

(56) References Cited

U.S. PATENT DOCUMENTS

| | | |
|---|---|---|
| 2010/0270178 A1 | 10/2010 | Guo et al. |
| 2013/0245401 A1* | 9/2013 | Estes ................ A61B 5/14532 |
| | | 600/309 |
| 2019/0346399 A1 | 11/2019 | Wu |
| 2020/0029876 A1 | 1/2020 | Brister et al. |
| 2020/0205701 A1 | 7/2020 | Bohm et al. |

OTHER PUBLICATIONS

U.S. Appl. No. 17/394,209, filed Aug. 4, 2021, Wu et al.
U.S. Appl. No. 17/394,191, filed Aug. 4, 2021, Wu.
International Search Report & Written Opinion of International Application No. PCT/EP2021/071740 dated Dec. 1, 2021.

* cited by examiner

CONTINUOUS ANALYTE MONITORING SENSOR CALIBRATION AND MEASUREMENTS BY A CONNECTION FUNCTION

This claims the benefit of U.S. Provisional Patent Application No. 63/061,135, filed Aug. 4, 2020 and titled "CONTINUOUS ANALYTE MONITORING SENSOR CALIBRATION AND MEASUREMENTS BY A CONNECTION FUNCTION," U.S. Provisional Patent Application No. 63/061,152, filed Aug. 4, 2020 and titled "NON-STEADY-STATE DETERMINATION OF ANALYTE CONCENTRATION FOR CONTINUOUS GLUCOSE MONITORING BY POTENTIAL MODULATION," U.S. Provisional Patent Application No. 63/061,157, filed Aug. 4, 2020 and titled "EXTRACTING PARAMETERS FOR ANALYTE CONCENTRATION DETERMINATION," and U.S. Provisional Patent Application No. 63/061,167, filed Aug. 4, 2020 and titled "BIOSENSOR WITH MEMBRANE STRUCTURE FOR STEADY-STATE AND NON-STEADY-STATE CONDITIONS FOR DETERMINING ANALYTE CONCENTRATIONS," each disclosure of which is hereby incorporated by reference herein in its entirety for all purposes.

FIELD

This disclosure relates to continuous sensor monitoring of an analyte in a bodily fluid.

BACKGROUND

Continuous analyte sensing in an in-vivo or in-vitro sample, such as, e.g., continuous glucose monitoring (CGM), has become a routine sensing operation in the field of medical devices, and more specifically, in diabetes care. For biosensors that measure analytes in a whole blood sample with discrete sensing, such as, e.g., pricking a finger to obtain a blood sample, the sample's temperature and hematocrit of the blood sample may be major sources of error. However, for sensors deployed in a non-whole blood environment with relatively constant temperatures, such as sensors used in a continuous in-vivo sensing operation, other sensor error sources may exist.

Accordingly, improved apparatus and methods for determining glucose values with CGM sensors are desired.

SUMMARY

In some embodiments, a method of determining glucose values during continuous glucose monitoring (CGM) measurements includes providing a CGM device including a sensor, a memory, and a processor; applying a constant voltage potential to the sensor; measuring a primary current signal resulting from the constant voltage potential and storing the measured primary current signal in the memory; applying a probing potential modulation sequence to the sensor; measuring probing potential modulation current signals resulting from the probing potential modulation sequence and storing measured probing potential modulation current signals in the memory; determining an initial glucose concentration based on a conversion function and the primary current signal; determining a connection function value based on the primary current signal and a plurality of the probing potential modulation current signals; and determining a final glucose concentration based on the initial glucose concentration and the connection function value.

In some embodiments, a continuous glucose monitoring (CGM) device includes a wearable portion having a sensor configured to produce current signals from interstitial fluid; a processor; a memory coupled to the processor; and transmitter circuitry coupled to the processor. The memory includes a connection function based on primary current signals generated by application of a constant voltage potential applied to a reference sensor, and a plurality of probing potential modulation current signals generated by application of a probing potential modulation sequence applied between primary current signal measurements. The memory includes computer program code stored therein that, when executed by the processor, causes the CGM device to measure and store a primary current signal using the sensor and memory of the wearable portion; measure and store a plurality of probing potential modulation current signals associated with the primary current signal; determine an initial glucose concentration based on a conversion function and the primary current signal; determine a connection function value based on the primary current signal and a plurality of the probing potential modulation current signals; and determine a final glucose concentration based on the initial glucose concentration and the connection function value.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the invention. For example, although the description below is related to continuous glucose monitoring, the devices, systems, and methods described below may be readily adapted to monitoring other analytes, such as, e.g., cholesterol, lactate, uric acid, alcohol, or the like, in other continuous analyte monitoring systems.

BRIEF DESCRIPTION OF THE DRAWINGS

The drawings, described below, are for illustrative purposes and are not necessarily drawn to scale. The drawings are not intended to limit the scope of the disclosure in any way.

DETAILED DESCRIPTION

Figure 1:
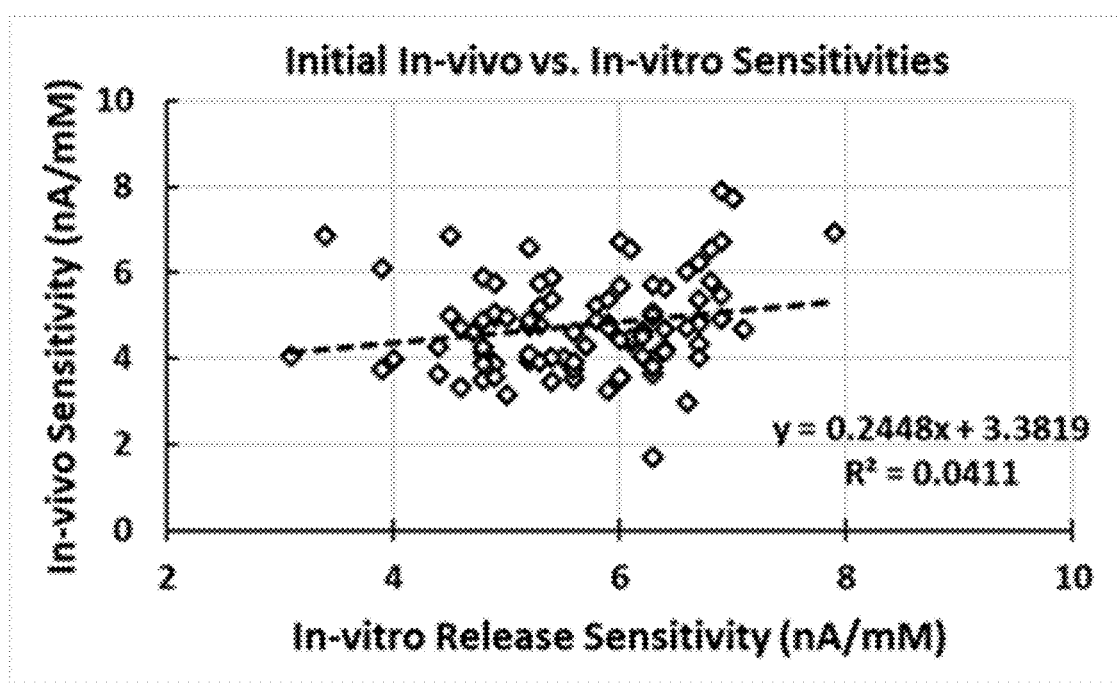
FIG. 1 illustrates in-vivo sensor sensitivity versus in-vitro sensor sensitivity in accordance with embodiments provided herein.

Reference will now be made in detail to example embodiments of the disclosure, which are illustrated in the accompanying drawings. Wherever possible, the same reference numbers will be used throughout the drawings to refer to the same or like parts. Features of the various embodiments described herein may be combined with each other, unless specifically noted otherwise.

The terms "voltage," "potential," and "voltage potential" are used herein interchangeably. "Currents," "signals," and "current signals" are also used herein interchangeably, as are "continuous analyte monitoring" and "continuous analyte sensing." As used herein, probing potential modulations (PPMs) refer to intentional changes made periodically to the otherwise constant voltage potential applied to a sensor during continuous analyte sensing, such as application of probing potential steps, pulses, or other potential modulations to the sensor.

Primary data points or primary currents refer to measurements of current signals generated in response to an analyte at a constant voltage potential applied to a sensor during continuous analyte sensing. Probing potential modulation (PPM) currents refer to measurements of current signals generated in response to probing potential modulations applied to the sensor during continuous analyte sensing. Reference sensors refer to sensors used to generate primary data points and PPM currents in response to reference glucose concentrations represented by blood glucose meter (BGM) readings, for example (e.g., primary currents and PPM currents measured for the purpose of determining prediction equations such as conversion and connection functions that are subsequently stored in a continuous analyte monitoring (CAM) device and used during continuous analyte sensing to determine analyte concentrations).

Likewise, reference sensor data points refer to the reference sensor readings at times closely corresponding to the times of the signals of the sensors in continuous operation. For example, reference data points may be obtained directly as the concentrations of reference analyte solutions prepared gravimetrically and verified by a reference sensor/instrument, such as a YSI glucose analyzer (from YSI Incorporated of Yellow Springs, Ohio), a Contour NEXT One (from Ascensia Diabetes Care US, Inc. of Parsippany, New Jersey), and/or the like, where the in-vitro study including a linearity study is carried out by exposing the continuous analyte sensors to the reference solutions. In another example, the reference sensor data points may be obtained from the readings of a reference sensor at periodic in-vivo measurements of the target analyte through samplings of venous blood draws or finger sticks.

Unity calibration refers to a mode of calibration where only one calibration sensitivity, or one of a few subsets of calibration sensitivities, is applied to all sensors at all times. Under unity calibration, in-situ finger stick calibrations or calibration with a sensor code may be minimized or no longer needed.

A connection function refers to a function established from in-vitro testing of multiple sensors/sensitivities to capture the variation range of sensor sensitivity, or a function established from combined in-vitro and in-vivo data to also capture the variation range of sensor sensitivity.

For sensors deployed in a non-whole blood environment with relatively constant temperatures, such as sensors used in a continuous in-vivo sensing operation, sensor error may be related to the sensor's short and long-term sensitivity and method of calibration thereafter. There are several problems/issues associated with such a continuous sensing operation: (1) the long break-in (warmup) time, (2) the factory or in-situ calibration, and (3) the change in sensitivity during the continuous sensing operation. These issues/problems are seemingly related to the sensor sensitivity as expressed in the initial decay (break-in/warmup time), the change in sensitivity due to the susceptibility of the sensor to the environment while in sensor production, and the environments/conditions in which the sensor is thereafter deployed.

According to one or more embodiments of the disclosure, apparatus and methods are operative to probe an initial starting condition of a continuous sensor operation for a sample analyte and to probe the sensor condition at any point thereafter during the sensor's continuous sensing operation.

Embodiments described herein include systems and methods for applying probing potential modulations on top of the otherwise constant voltage applied to an analyte sensor. The terms voltage, potential, and voltage potential are used herein interchangeably.

Methods are provided of formulating parameters for prediction equations that may be employed to accurately determine analyte concentrations continuously from an analyte sensor. In some embodiments, predictions equations may include a conversion function and a connection function, as described below. Furthermore, a method of and apparatus for determining analyte concentrations are provided with the use of probing potential modulation (PPM) self-sufficient signals (e.g., working electrode currents resulting from the application of probing potential modulations). Such methods and apparatus may allow analyte concentration determinations while (1) overcoming the effects of different background interfering signals, (2) levelling or removing the effects of different sensor sensitivities, (3) shortening the warmup time at the beginning of a (long-term) continuous monitoring process, and/or (4) correcting sensor sensitivity changes over the continuous monitoring process. These and other embodiments are described below with reference to FIGS. 1-13D.

For a continuous glucose monitoring (CGM) biosensor, which is usually operated with a constant applied voltage, the currents from the mediator are measured continuously as a result of the enzyme oxidation of the target analyte glucose. In practice, currents are typically measured or sensed every 3 to 15 minutes or at another regular interval despite being referred to as continuous. There is an initial break-in time when the CGM sensor is first inserted/implanted into a user, which may last from 30 minutes to several hours. Once the CGM sensor is broken-in, its sensitivity may still change for various reasons. Thus, there is a need to sense the sensor's operating condition during its initial and after break-in times to identify any changes in its sensitivity.

The CGM sensor operation starts with the applied voltage $E_0$ after it is inserted/implanted subcutaneously into a user. The applied voltage $E_0$ is usually at a point on the redox plateau of the mediator. For the natural mediator of oxygen with the enzyme of glucose oxidase, the oxidation plateau of hydrogen peroxide $H_2O_2$ (the oxidation product of the enzyme reaction) ranges from about 0.5 to 0.8 volts versus an Ag/AgCl reference electrode in a media of about 100-150 mM chloride concentration. The operation potential for the glucose sensor may be set at 0.55-0.7 volts, which is within the plateau region.

Embodiments described herein employ probing potential modulations as periodic perturbations to the otherwise constant voltage potential applied to the working electrode of a subcutaneous biosensor in a continuous sensing operation (e.g., for monitoring biological sample analyte such as glucose). During a continuous sensing operation, such as continuous glucose monitoring, sensor working electrode current is typically sampled every 3-15 minutes (or at some other frequency) for glucose value determinations. These current measurements represent the primary currents and/or primary data points used for analyte determinations during continuous sensing operation. In some embodiments, periodic cycles of probing potential modulations may be employed after each primary current measurement so that a group of self-sufficient currents accompanies each primary data point with information about the sensor/electrode status and/or condition.

Probing potential modulations may include one or more steps in potential that are different than the constant voltage potential normally used during continuous analyte monitoring. For example, probing potential modulations may include a first potential step above or below the constant voltage potential, a first potential step above or below the constant voltage potential and then a potential step returning to the constant voltage potential, a series of potential steps above and/or below the constant voltage potential, voltage steps, voltage pulses, pulses of the same or different durations, square waves, sine waves, triangular waves, or any other potential modulations.

As described, conventional biosensors used in continuous analyte sensing are operated by applying a constant potential to the working electrode (WE) of the sensor. Under this condition, the currents from the WE are recorded periodically (e.g., every 3-15 minutes or at some other time interval). In this way, biosensors generate currents that are only attributable to changes in analyte concentrations, not changes in applied potential. That is, non-steady-state currents associated with the application of different potentials are avoided or minimized. While this approach simplifies the continuous sensing operation, the current signals in the data stream from application of a constant potential to the sensor provide minimum information about the sensor status/condition. That is, sensor current signals from application of a constant potential to a sensor provide little information relevant to issues associated with long-term continuous monitoring by the sensor, such as lot-to-lot sensitivity variations, the long warmup time due to initial signal decay, sensor sensitivity changes over a long-term monitoring process, effects from varying background interfering signals, or the like.

Embodiments described herein include systems and methods for applying probing potential modulations on top of the otherwise constant voltage applied to an analyte sensor. Methods are provided for formulating parameters for prediction equations, which may include a conversion function and a connection function, that may be employed to accurately determine analyte concentrations continuously from an analyte sensor. For example, in some embodiments, a conversion function may be applied to a raw glucose signal (e.g., working electrode current or working electrode current minus background current) to determine an initial glucose value, and a connection function may then be applied to the initial glucose value to determine a final glucose value.

Continuous glucose monitoring (CGM) sensors implanted subcutaneously require timely calibrations against a reference glucose value. Conventionally, the calibration process involves taking a blood glucose monitoring (BGM) reading from a finger stick glucose measurement, or the capillary glucose value and entering the BGM value into the CGM device to set the CGM sensor's calibration point for the next operation period. Usually, this calibration process is performed on a daily basis, or at least one finger stick glucose measurement per day as the CGM sensor's sensitivity may change from day to day. This is an inconvenient but necessary step to ensure the accuracy of the CGM sensor system.

To improve the usability and to minimize the number of the finger stick BGM tests, a logical step would be to link an individual sensor's in-vitro sensitivity to in-vivo sensitivity one-by-one with some relationship. However, in practice, a correlation between in-vitro and in-vivo sensitivity for individual sensors is difficult to observe and complex. This is not a surprise as sensor sensitivity changes vary with time and under different conditions during CGM. Additionally, sample types in in-vitro testing and in-vivo testing are different. For in-vitro tests, the sample type is either a glucose solution in a buffer or, at best, a simulated interstitial fluid (ISF), while for in-vivo tests, the sample type is interstitial fluid with reference to capillary glucose. A more robust connection is desired between in-vitro and in-vivo glucose measurements that keeps finger stick BGM measurements for calibrations at a minimum.

Embodiments of the present disclosure provide methods of unity calibration and methods of making a connection between in-vitro and in-vivo analytes for continuous monitoring sensors implanted subcutaneously (under the skin of a subject) without additional calibrations. For example, in some embodiments, the present disclosure provides a connection of in-vitro and in-vivo glucose for continuous monitoring sensors implanted subcutaneously.

In one or more embodiments, a method of determining continuous glucose values is provided by unity calibration from sensors with linear and non-linear responses, sensors with normally hydrated membrane conditions, sensors with rapidly changing membranes and/or environmental conditions, and/or sensors with unbalanced enzyme-mediator conditions. In some embodiments, a method is provided of determining glucose concentrations against reference capillary glucose through a simple conversion function, a connection function and, in some embodiments, a final adjustment function. In yet other embodiments, the adjustment for the connection function with regard to in-vivo sensor behaviors is embedded in the process of deriving the connection function by combining in-vitro and in-vivo data. Further, a biosensor system for continuous glucose monitoring is provided with a membrane covered biosensor and a device operated under the probing potential modulation as described herein.

As described above, unity calibration is highly desirable, and may be done by projecting the in-vivo sensitivity from the in-vitro sensitivity for individual sensors, reducing/removing the need for finger stick calibrations during a CGM operation. In such pursuit of a one-to-one corresponding relationship between the in-vitro and in-vivo sensitivities, the individual sensitivities of sensors from in-vitro release tests were tracked in a clinical study to establish a correlation to initial in-vivo sensitivities. It was found that such one-to-one correlation between in-vitro and in-vivo sensitivities was virtually non-existent ($R^2$ value of 0.04), as shown in FIG. 1, which illustrates in-vivo sensor sensitivity versus in-vitro sensor sensitivity in accordance with embodiments provided herein.

Figure 2A:
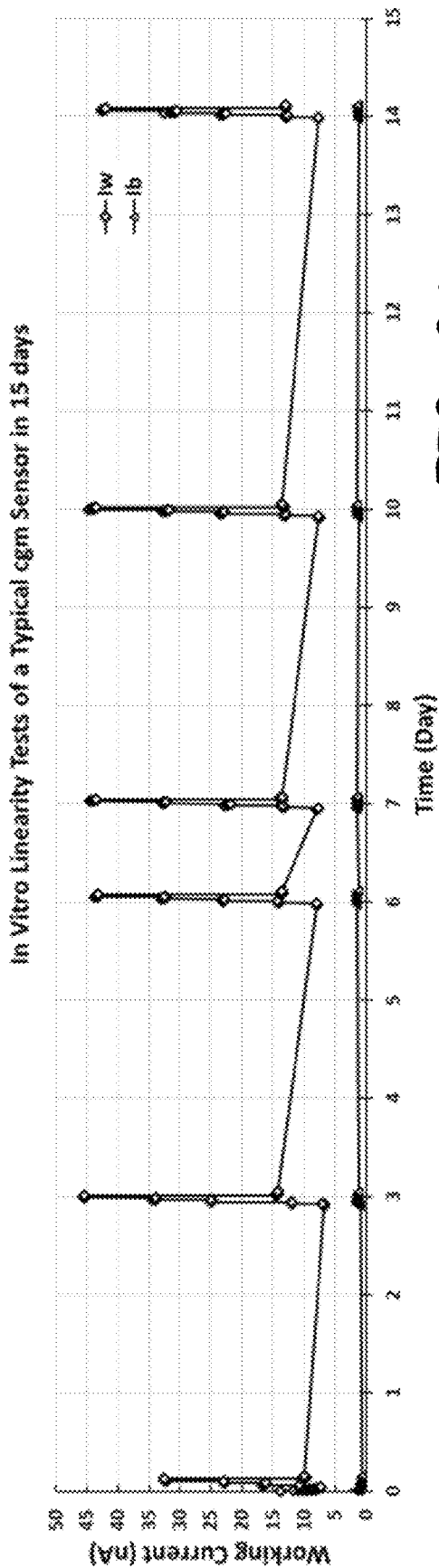
FIG. 2A illustrates linearity tests in working electrode (Iw) currents over 15 days, in accordance with embodiments provided herein.
Figure 2B:
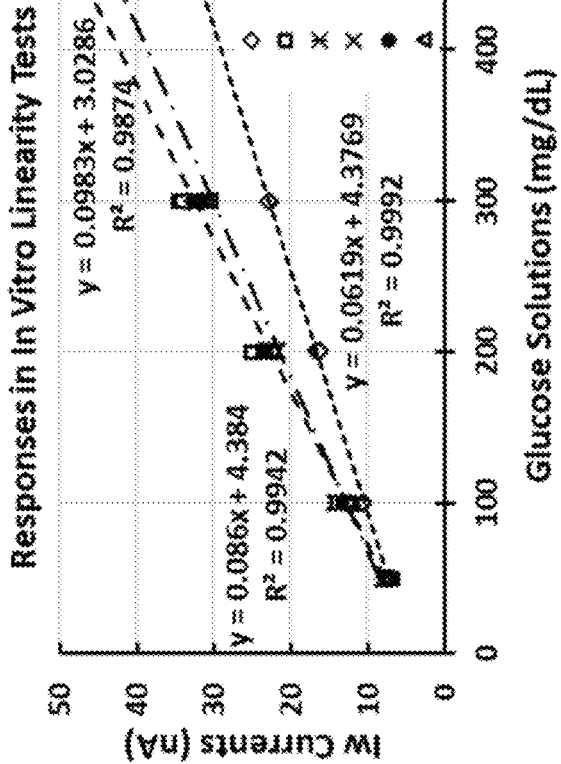
FIG. 2B illustrates responses of linearity tests in working electrode (Iw) currents for glucose solutions of 50, 100, 200, 300 and 450 mg/dL, in accordance with embodiments provided herein.

Even if there is some correlation with a finite $R^2$ value (say 0.5), the sensitivity change over time would still make the one-to-one corresponding sensitivity from in-vitro to in-vivo unpredictable. Such sensitivity change can be seen in FIGS. 2A and 2B for six in-vitro linearity tests over 15 different days. FIG. 2A illustrates linearity tests in working electrode (Iw) currents over 15 days, and FIG. 2B illustrates responses of linearity tests in Iw currents for glucose solutions of 50, 100, 200, 300 and 450 mg/dL, in accordance with embodiments provided herein.

The sensitivities in the subsequent linearity tests are higher than that in the day 1 test by 35-45%. Thus, even if the initial in-vivo sensitivity can be predicted from the in-vitro sensitivity, the subsequent sensitivity change would still warrant in-situ finger stick calibrations in a continuous monitoring operation.

The above two examples illustrate that it is desirable to establish a method of unity calibration which provides outcomes for continuous analyte sensing by a reliable and predictable connection from in-vitro glucose to in-vivo glucose, preferably having no finger stick calibrations during a continuous glucose monitoring session. Embodiments described herein include systems and methods that connect in-vitro glucose to in-vivo glucose by applying probing potential modulations on top of the otherwise constant voltage applied to an analyte sensor. Methods are provided for formulating parameters for a prediction equation (e.g., a conversion and/or a connection function) that may be employed to accurately determine analyte concentrations continuously from an analyte sensor.

In some embodiments, a CGM sensor may include four electrodes, including working, blank (or background), reference and the counter electrodes enclosed in a membrane structure. The working electrode is adhered to and covered with a layer of cross-linked enzyme, such as glucose oxidase, which is not part of the outer membrane structure and which functions to catalyze the oxidation of the target analyte glucose. The blank electrode provides background signals (background current Ib) from all oxidizable chemical species at the same operating potential as the working electrode. Thus, the difference current (Iw−Ib) between the two electrode currents Iw and Ib serves as the analyte responsive signal, effectively removing the background/interferent signal component through subtraction of Ib. The reference electrode provides a potential reference for the working and the blank electrodes while the counter electrode serves to carry out all counter redox reactions of the working and blank electrodes to complete the electrochemical reaction. In some embodiments, current signals Iw from a working electrode may be used alone, when the membrane structure provides the function of rejecting the interference species. In yet other embodiments, the function of rejecting the interference signals is embedded in the algorithm through the PPM signals and the primary signals from working electrode current Iw without subtracting the background current signals Ib.

In one or more embodiments, a probing potential modulation (PPM) sequence generated from a CGM transmitter may be applied to the working and the blank electrodes of a CGM sensor simultaneously, and Iw and Ib currents may be sampled. For example, Iw and/or Ib currents may be sampled for each primary data point every 3 minutes of repeated cycles, and every 2 seconds during a PPM cycle, resulting in the Iw and Ib primary currents and Iw and Ib PPM currents. Other sampling rates for primary and/or PPM currents may be used. In one or more embodiments, the ratio of the PPM time (the total time of the PPM sequence) to the entire one cycle time (3 minutes in this case) may be between about 0.05-0.5, and in some embodiments about 0.1-0.2. Other ratios of PPM time to entire cycle time may be employed.

Figure 3A:
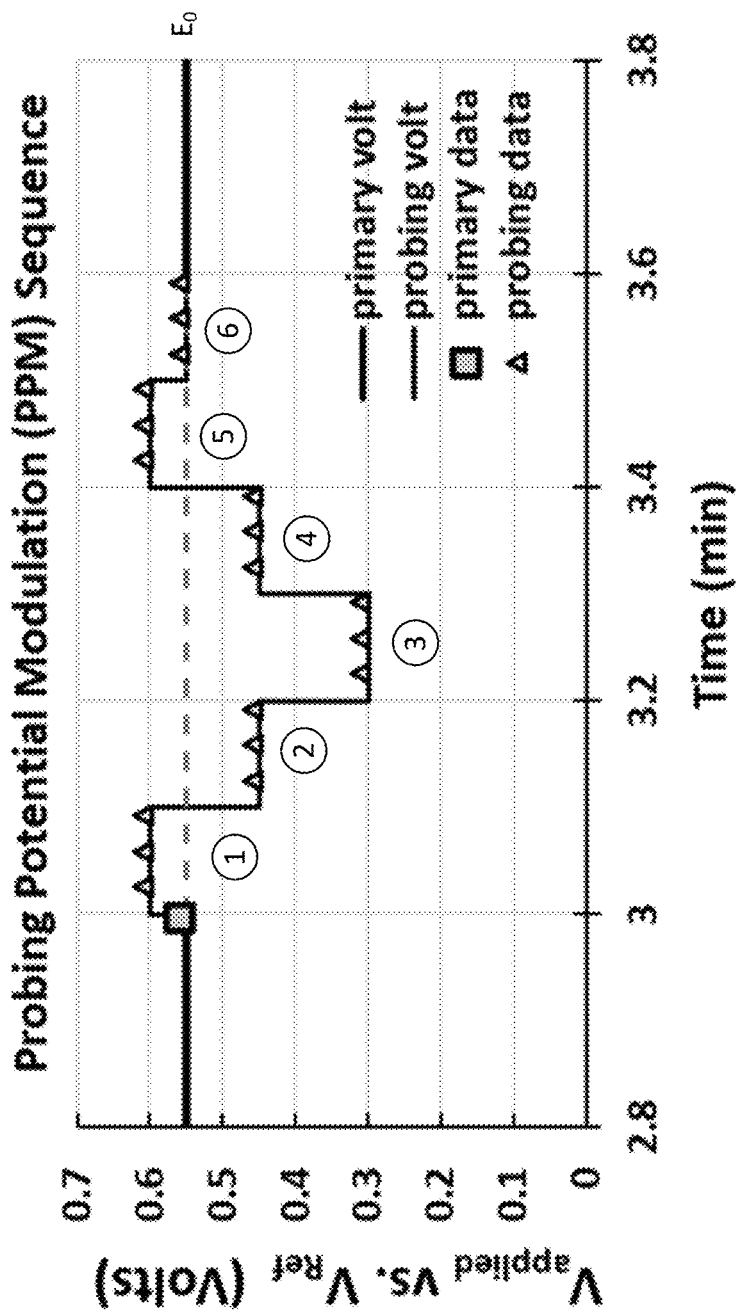
FIG. 3A illustrates applied voltages and timing of current sampling in one example probing potential modulation (PPM) cycle in accordance with embodiments provided herein.
Figure 3B:
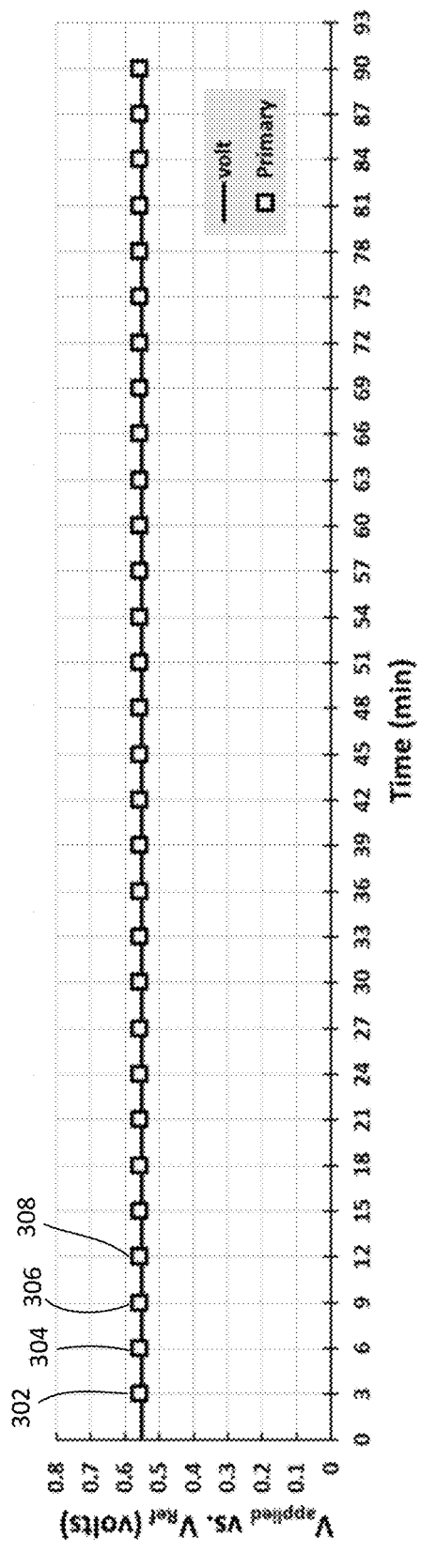
FIG. 3B illustrates an example constant applied voltage, and example timing of taking current measurements for individual primary data points in accordance with embodiments provided herein.
Figure 3C:
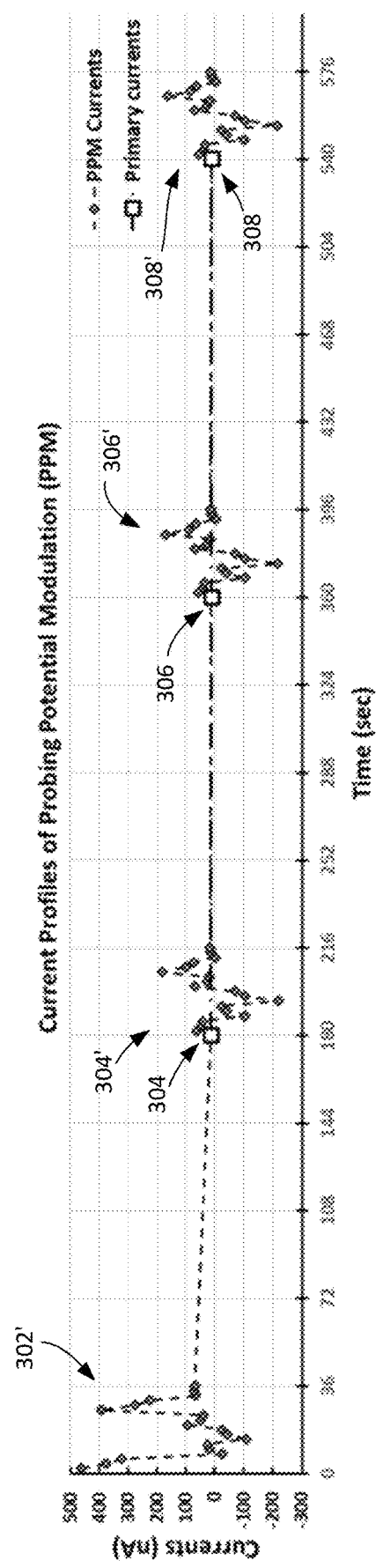
FIG. 3C illustrate output currents (the temporal current profile) of the first four cycles for the primary data points and the PPM currents resulting from the constant applied voltage of FIG. 3B and PPM cycles of FIG. 3A in accordance with embodiments provided herein.
Figure 3D:
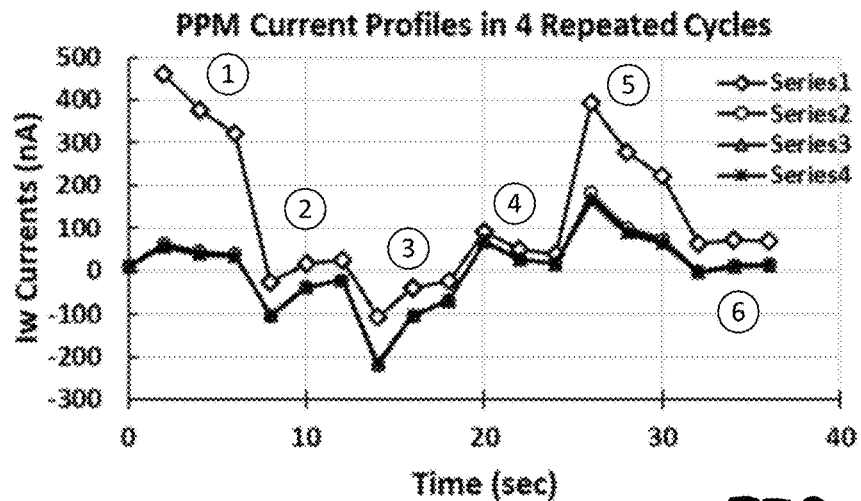
FIGS. 3D and 3E illustrate the superimposed PPM working electrode current Iw and PPM blank electrode current Ib, respectively, from the first four PPM cycles shown in FIG. 3C in accordance with embodiments provided herein.
Figure 3E:
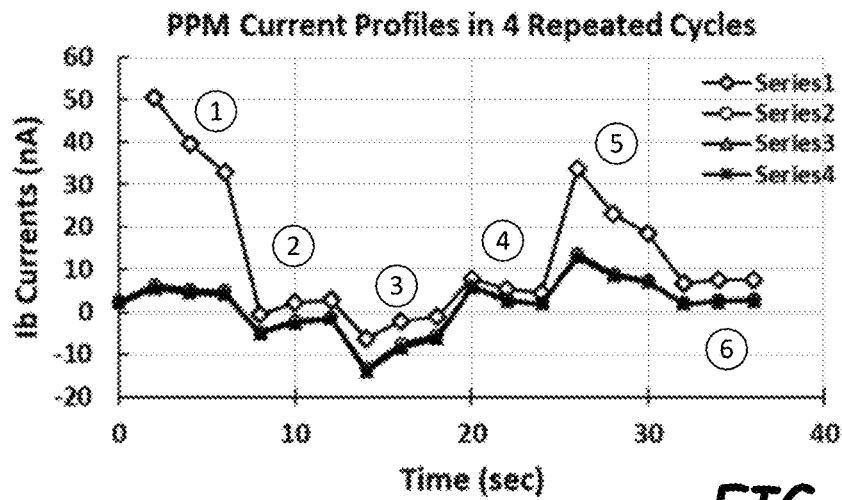
Figure 3F:
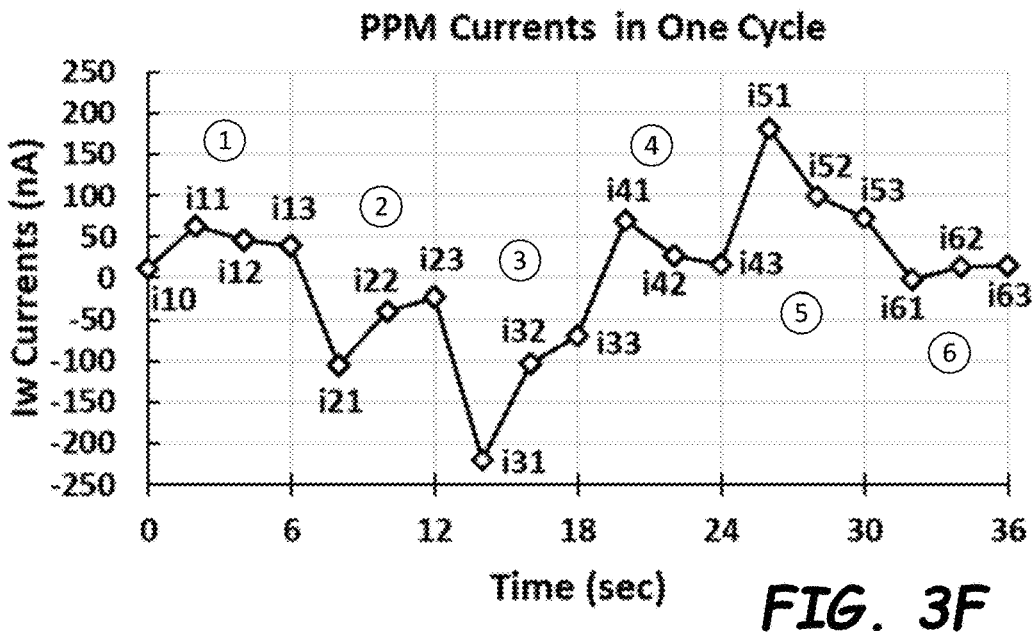
FIG. 3F illustrates example timing and labels of measured PPM currents in one cycle in accordance with embodiments provided herein.

FIG. 3A illustrates applied voltages and timing of current sampling in one example PPM cycle or sequence in accordance with embodiments provided herein. In FIG. 3A, the example PPM sequence has six voltage potential steps 1-6. Other numbers, values or types of voltage potential changes may be used. FIG. 3B illustrates an example constant applied voltage, and example timing of taking current measurements for individual primary data points in accordance with embodiments provided herein (e.g., every 3-5 minutes, for example). The squares on FIG. 3B illustrate the timing at which primary current signals, such as Iw and Ib, are sampled under the constant applied voltage. The first four cycles of sampling are labelled 302, 304, 306 and 308, respectively. FIG. 3C illustrate output currents (the temporal current profile) of the first four cycles for the primary data points and the PPM currents (labelled 302', 304', 306' and 308', respectively) resulting from the constant applied voltage of FIG. 3B and PPM cycles of FIG. 3A in accordance with embodiments provided herein. FIGS. 3D and 3E illustrate the superimposed PPM working electrode current Iw and PPM blank electrode current Ib from the first four PPM cycles shown in FIG. 3C in accordance with embodiments provided herein. The numbered circles in FIGS. 3D and 3E correspond to the six voltage potential steps in the example PPM sequence of FIG. 3B. Finally, FIG. 3F illustrates example timing and labels of measured PPM currents in one cycle in accordance with embodiments provided herein. The numbered circles in FIG. 3F corresponds to the six voltage potential steps in the example PPM sequence of FIG. 3B.

In some embodiments, the PPM sequence in the first cycle 302' triggers the recording of currents 2 seconds after the sensor is started by the CGM system. That is, the PPM sequence is applied before the first primary data point is recorded at 3-minute. As shown in FIGS. 3D and 3E, both the PPM Iw and Ib currents in the first cycle are substantially higher than the PPM currents in the later cycles. In addition, the currents on step 1 and step 5 of the first cycle are disproportionally higher than currents in other PPM steps in comparison to other PPM currents in the non-starting condition. This behavior serves well as an indicator of the starting condition of a CGM sensor.

In pursuit of a connection between the in-vitro and in-vivo glucose, a set of linearity tests from different CGM sensors was conducted at various points throughout the course of 15 days. The target glucose concentrations were 50, 100, 200, 300 and 450 mg/dL in the glucose solutions with the added concentration of 0.2 mg/dL of acetaminophen as the surrogate interference species of a normal interference level for the in-vitro tests. Utilizing currents from the blank electrode representing the interference signals, the current difference (Iw−Ib) is used as the glucose responsive signal, which is plotted in FIG. 4A for all sensor currents from the linearity tests. Specifically, FIG. 4A illustrates composite CGM sensor responses from in-vitro linearity tests of varying sensor sensitivities of various sensors (e.g., 10 sensors) in accordance with embodiments provided herein.

Figure 4A:
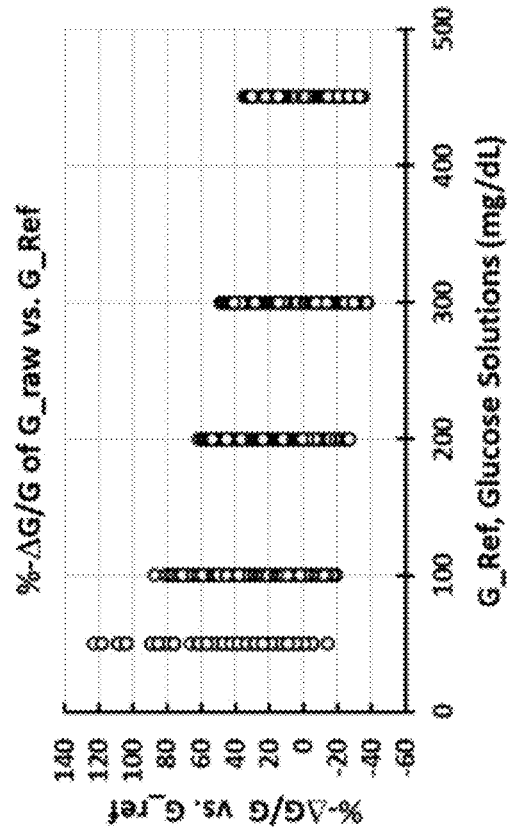
FIG. 4A illustrates working electrode current (minus background current) versus reference glucose concentration for 10 sensors in accordance with embodiments provided herein.

As shown in FIG. 4A, the glucose response signals (the primary data points) from all sensors tested at different times of the 15-day in-vitro continuous monitoring spread out in a wide range. The current response range is centered at the regression line of $(Iw-Ib)=0.0965*G_{ref}$ going through zero where the response population is approximately defined by two lines of 0.0667 to 0.1778 nA/mg/dL. It can be seen that the upper line has a slope that is about three times that of the lower line in the combined responses. One of such responses can be seen in FIG. 2B from one of the sensors tested with an initial low response followed by increased responses at the later tests.

Given the uncertainty of making the one-to-one correlation between the in-vitro and in-vivo sensitivities, a method of making a connection from in-vitro to in-vivo glucose is disclosed herein by applying a unified "conversion function" to the data of wide range of sensor responses, followed by a "connection function" to reduce glucose error to a narrow band. The unified conversion function computes raw or "initial" glucose values $G_{raw}$=f(signal), where signal is the measured current signal and f may be a linear or non-linear function. When the conversion function f is non-linear, then sensitivity or response slope is not applied (as described below).

In its simplest form, a unified conversion function may be a linear relationship between measured current signals and reference glucose levels obtained from in-vitro test data. For example, a unified conversion function may be a linear relationship between the glucose signal (e.g., Iw-Ib), a slope and reference glucose $G_{ref}$:

$$\text{Signal}=\text{slope}*G_{ref} \qquad (1)$$

such that, $$G_{ref}=\text{signal}/\text{slope} \qquad (2)$$

where slope represents a composite slope ($\text{slope}_{composite}$), also referred to as a unified composite slope, selected based on the in-vitro sensor data as described below. The above relationship may then be used to calculate an initial or raw glucose concentration $G_{raw}$ during CGM:

$$G_{raw}=\text{Signal}/\text{slope}_{composite} \qquad (3)$$

In some embodiments, rather than using a linear conversion function, a non-linear conversion function, such as a polynomial, may be employed (e.g., to better fit the varied responses of sensors).

Figure 4C:
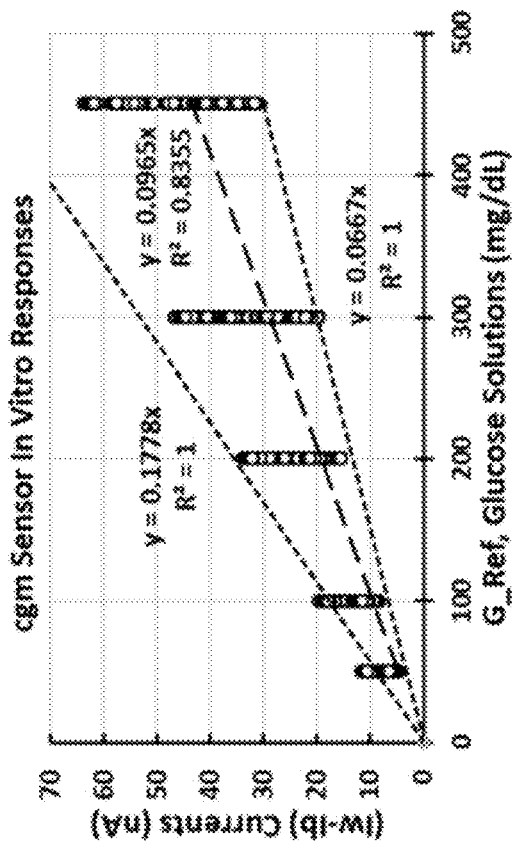
FIG. 4C illustrates the output (final) glucose concentration from FIG. 4B using a connection function with unity calibration, in accordance with embodiments provided herein.
Figure 4B:
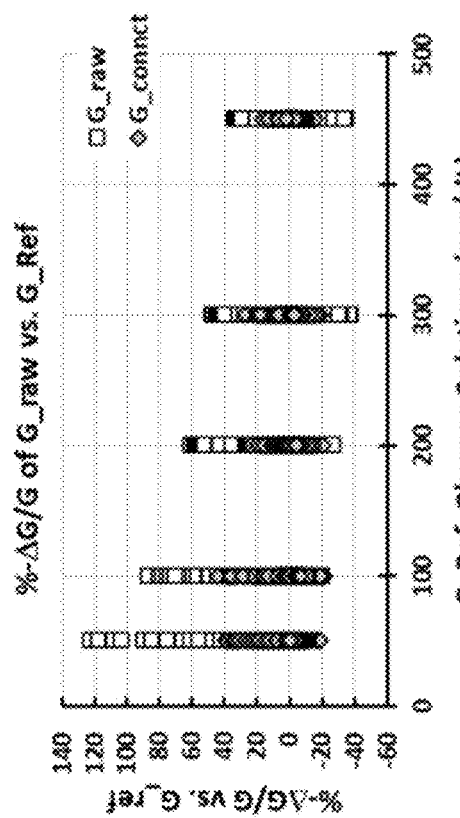
FIG. 4B illustrates a distribution plot of relative error (%-bias) of raw glucose concentration with unity calibration, in accordance with embodiments provided herein.
Figure 4D:
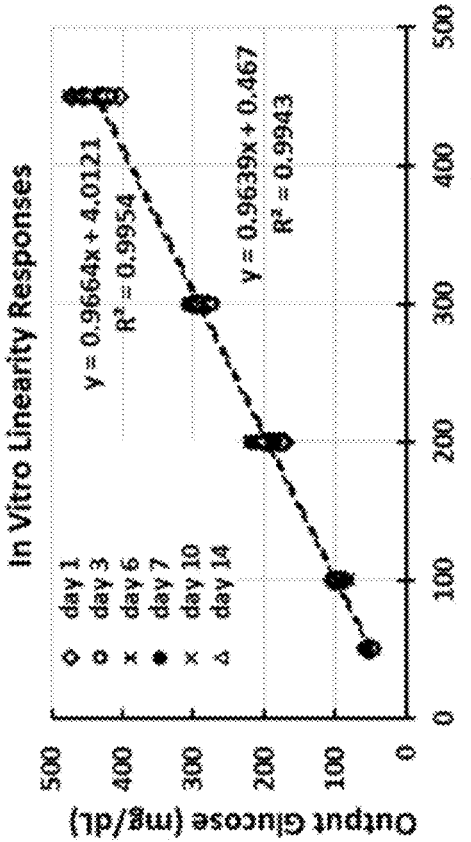
FIG. 4D illustrates a comparison of %-biases for $G_{raw}$ and $G_{connect}$ from data in FIG. 4A in accordance with embodiments provided herein.

Additional details are now described with reference to FIGS. 4B-4D, in which FIG. 4B illustrates a distribution plot of relative error (%-bias) of raw glucose concentration, $G_{raw}$=(Iw−Ib)/$S_{composite}$, in accordance with embodiments provided herein. FIG. 4C illustrates the output glucose from FIG. 4B using a connection function in accordance with embodiments provided herein. FIG. 4D illustrates a comparison of %-biases for $G_{raw}$ and $G_{connect}$ from data in FIG. 4A in accordance with embodiments provided herein.

FIG. 4B shows the %-bias distribution for $G_{raw}$ computed using a $\text{slope}_{composite}$ of 0.1333. This composite slope is preselected to be higher than 0.0965 from the center of the data population as shown in FIG. 4A (e.g., based on linear regression), and is based on the consideration of providing overlap coverage between two subsets of the entire response population per sensors' manufacturing specification. The unified composite slope to compute $G_{raw}$ makes the %-bias values spread out more as there is no one-to-one corresponding slope to calculate glucose for each sensor, and nor are there individual slopes for the later responses during the 15-day monitoring. However, a single conversion makes the in-vitro to in-vivo connection a simple matter without calibrations, if a connection function is applied to the individual error (% bias=$100\%*\Delta G/G=100\%*(G_{raw}-G_{ref})/G_{ref}$) to obtain the narrow band of glucose. This connection function is derived from the PPM parameters based on the $\Delta G_{raw}/G_{ref}$ values. By way of such narrowing the error band from the $G_{raw}$ data, the connection function is referred as a connection function making connection from in-vitro to in-vivo sensing without calibrations, meaning accommodating all responses of sensors to a narrow band of error.

A connection function is said to be a broad scope connection from in-vitro glucose to in-vivo glucose when the connection function provides the predicted in-vivo glucose values to a narrow band of error without calibration. In this context, it is not seeking to establish the one-to-one corresponding relationship for the in-vitro sensitivity and in-vivo sensitivity (for a particular sensor). Instead, the connection function provides glucose values from sensors within a large sensitivity range as long as the sensors are responsive to glucose. The responses may be linear, or non-linear.

Taking advantage of the rich information about the CGM sensors from PPM currents, this connection function is derived from PPM currents and associated parameters (including in some cases primary currents responsive to a constant applied voltage). When each response data point at the periodic cycle is converted by a composite conversion function to a glucose value $G_{raw}$, there is an error or %-bias associated with it $\Delta G/G_{raw} = (G_{raw} - G_{ref})/G_{ref}$. By setting $G_{connect} = G_{ref}$ then:

$$G_{connect} = G_{raw}/(1 + \Delta G/G_{raw}) = G_{raw}/(1 + \text{connection function}) \quad (4)$$

where connection function=$\Delta G/G_{raw}$=f(PPM parameters). One way for deriving the connection function is by setting the relative error $\Delta G/G_{raw}$ as the target of the multi-variate regression with input parameters from the PPM parameters. The application of the PPM method onto a CGM sensor system and the resulted PPM currents are shown in FIGS. 4C and 4D. In FIG. 4C, output glucose refers to the final glucose concentration, $G_{connect}$, after application of the connection function.

To summarize, in some embodiments, the primary current i10 (e.g., Iw-Ib) may be used as part of a conversion function to convert a raw current signal to a raw or initial glucose value $G_{raw}$. For example, $G_{raw}$ may be computed as:

$$G_{raw} = (Iw-Ib)/0.1333 \quad (5)$$

Other relationships between $G_{raw}$ and the primary current may be used.

Once $G_{raw}$ is known, a connection function may then be employed to compute a compensated or final glucose signal or concentration, $G_{comp}$ (also referred to as $G_{connect}$). For example, the connection function may be derived from in-vitro data using steady-state signals (primary current i10) and non-steady-state signals (PPM signals) as input parameters and relative error $\Delta G/G_{raw}$ as the target for multivariate regression.

In one embodiment, a connection function is provided by $G_{connect} = G_{raw}/(1+ \text{connection function})$, where connection function=f(PPM parameters) derived by multivariate regression, such that the error deviated from the composite conversion function, such as the Slope$_{composite}$, is reduced/minimized to produce glucose values within a narrow band of error. In another embodiment, the connection function is simply a prediction equation by setting the $G_{Ref}$ as the regression target with multivariate regression from the PPM input parameters. An example connection function CF is provided below. It will be understood that other numbers and/or types of terms may be used.

$\Delta G/G_{raw}$=−5.838261−3.511979*$z53$+6.5e−6*$GR6$−
0.005973*$GR53$+0.012064*$Gz61$−
0.005874*$Gy52$−0.038797*$Gy43$−
14.75114*$R63R51$+0.385802*$R64R43$−
6.134046*$R65R52$+0.059922*$R51R43$−
0.009478*$GR54R42$−31.22696*$z61z32$+
7.036651*$z63z42$−5.153158*$z64z42$−
10.93096*$z65z54$−1.981203*$z51z31$+
1.578947*$z51z21$ \quad (6)

Where $GR6 = G_{raw}*R6$, $Gz61 = G_{raw}*z61$, $Gy52 = G_{raw}*y52$, and $R63R51 = R63/R51$, $R64R43 = R64/R43$, $z64z42 = z64/z42$, etc., as described further below. Many other PPM currents and/or parameters may be used.

Example PPM Currents and PPM Parameters

Example PPM current labeling as shown in FIG. 3F, in which the first digit of the ixy format denotes the potential step number (1-6) while the second digit denotes which sampled current within the potential step is employed (1-3). For example, i10 denotes the primary current; i11 is the first current of the three recorded currents in step 1 while i13 is the third current of the three recorded currents in step 1. Similarly, i63 is the third current of the three recorded currents in step 6. Additional parameters are provided below.

Rx parameters: The general format of these parameters is given by the ending current being divided by the first current within one step. For example, R1=i13/i11, R2=i23/i21, R3=i33/i31, R4=i43/i41, R5=i53/i51, and R6=i63/i61.

Xij parameters: The general format for this type of parameter is given by the ending current of a later potential step being divided by the ending current of an earlier step. For example, parameter x61 is determined by i63/i13 where i63 is the ending current of potential step 6 in the three recorded currents per step while i13 is the ending current of step 1. For example, x61=i63/i13, x62=i63/i23, x63=i63/i33, x64=i63/i43, x65=i63/i53, x51=i53/i13, x52=i53/i23, x53=i53/i33, x54=i53/i43, x41=i43/i13, x42=i43/i23, x43=i43/i33, X31=i33/i13, x32=i33/i23, and X21=i23/i13.

Yij parameters: The general format for this type of parameter is given by the ending current of a later step being divided by the first current of an earlier step. For example, parameter y61 is determined by i63/i11 where i63 is the ending current of step 6 in the three recorded currents per step while i11 is the first current of step 1. For example, y61=i63/i11, y62=i63/i21, y63=i63/i31, y64=i63/i41, y65=i63/i51, y51=i53/i11, y52=i53/i21, y53=i53/i31, y54=i53/i41, y41=i43/i11, y42=i43/i21, y43=i43/i31, y31=i33/i11, y32=i33/i21, and y21=i23/i11.

Zij parameters: The general format for this type of parameter is given by the first current of a later step being divided by the ending current of an earlier step. For example, parameter z61 is determined by i61/i13 where i61 is the first current of step 6 in the three recorded currents per step while i13 is the ending current of step 1. For example, z61=i61/i13, z62=i61/i23, z63=i61/i33, z64=i61/i43, z65=i61/i53, z51=i51/i13, z52=i51/i23, z53=i51/i33, z54=i51/i43, z41=i41/i13, z42=i41/i23, z43=i41/i33, z31=i31/i13, z32=i31/i23, and z21=i21/i13.

Wij parameters: The general format for this type of parameters is given by the middle current of a later step being divided by the middle current of an earlier step. For example, parameter w61 is determined by i62/i12 where i61 is the middle current of step 6 in the three recorded currents per step while i12 is the ending current of step 1. For example, w61=i62/i12, z62=i62/i22, z63=i62/i32, z64=i62/i42, z65=i62/i52, w51=i52/i12, z52=i52/i22, z53=i52/i32, z54=i52/i42, w41=i42/i12, z42=i42/i22, z43=i42/i32, w31=i32/i12, z32=i32/i22, and w21=i22/i12.

Additional PPM parameters may include the normalized PPM currents ni11=i11/i10, ni12=i12/i10, . . . , ni63=i63/ i10, the relative differences $d11=(i11-i12)/i10$, $d12=(i12-i13)/i10$, $d21=(i21-i22)/i10$, $d22=(i22-i23)/i10$, ..., $d61=(i61-i62)/i10$, and $d62=(i62-i63)/i10$, the average currents of each PPM potential step $av1=(i11+i12+i13)/3$, $av2=(i21+i22+i23)/3$, ... and their ratios $av12=av1/av2$, etc.

Other types of parameters, such as the PPM current differences or relative differences carrying the equivalent or similar information, may also be used. For demonstrating the feasibility of overcoming the issues of different sensor sensitivities, the initial warmup time, the sensitivity changes over the long-term, and the different background signals due to the intake of different amounts of interfering substances, the above parameters, along with their temperature cross terms, may be the inputs in the multi-variate regression in its simple form. Additional terms/parameters may be provided in the regression.

Figure 5B:
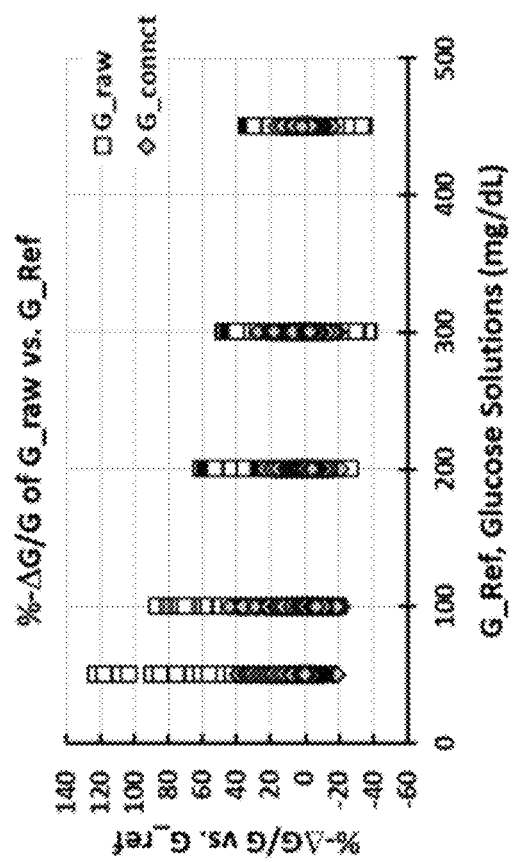
FIG. 5B illustrates a comparison of %-biases for $G_{raw}$ and $G_{connect}$ from data in FIG. 4A after employing a connection function, in accordance with embodiments provided herein.
Figure 5A:
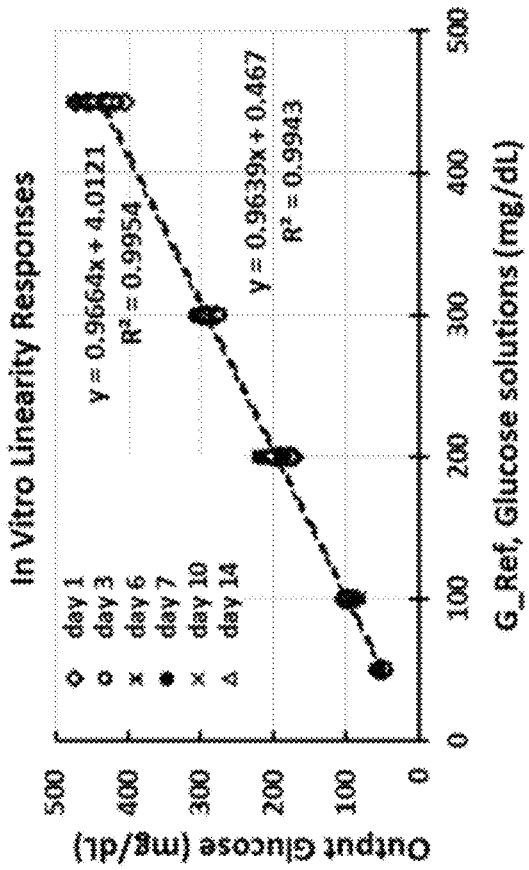
FIG. 5A illustrates the output glucose concentration data of FIG. 2B after employing a connection function with unity calibration, in accordance with embodiments provided herein.
Figure 6:
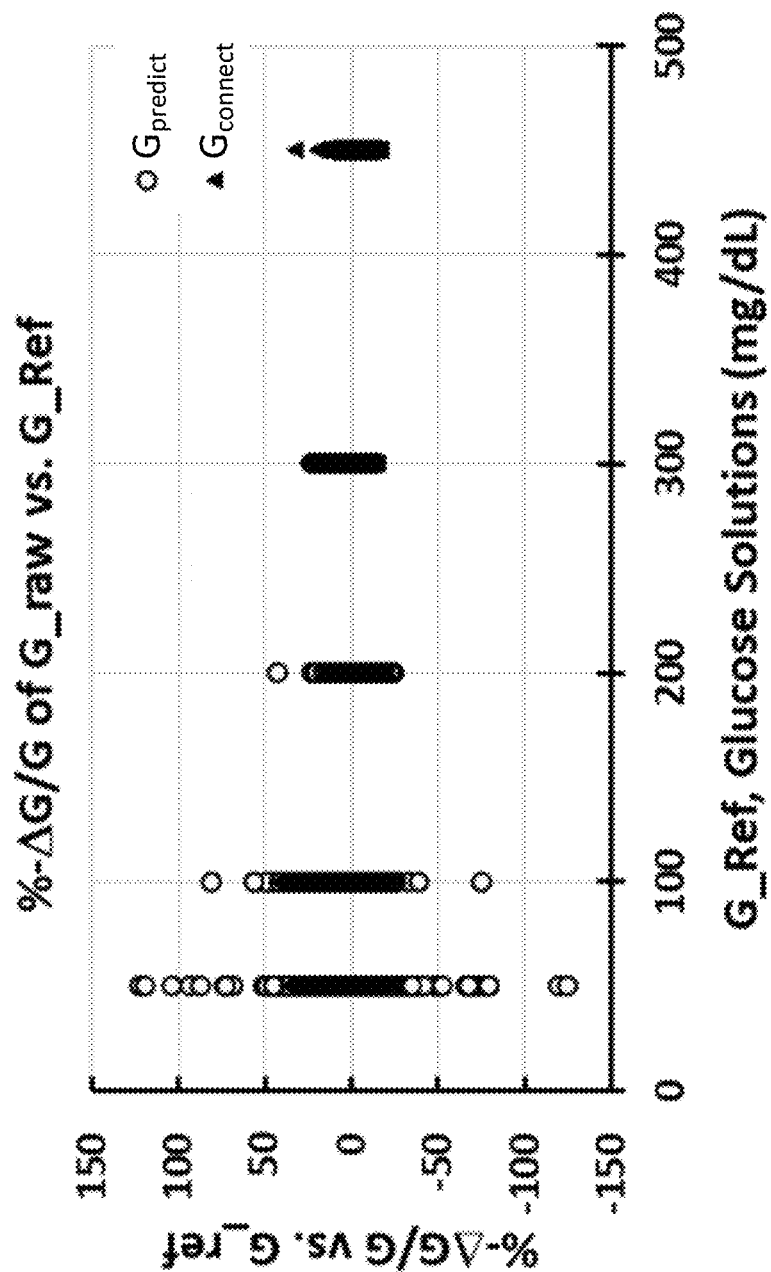
FIG. 6 illustrates a comparison of the relative error in glucose %-ΔG/G by a single prediction equation versus the use of a conversion function with unity calibration followed by a connection function for the same data set, in accordance with embodiments provided herein.

Using the connection function approach, FIG. 5A shows that the uneven responses shown in FIG. 2B are made to collapse into essentially one output glucose response line without having to consider the individual response sensitivities. What this means is that the future sensitivities and their variation thereof are immaterial as long as the sensor produces the signals responsive to glucose within a range of responses. This in effect serves the function of providing glucose determinations without having to calibrate the sensor. This method is further applied to A large data set of in-vitro linearity tests from the 10 CGM sensors shown in FIG. 4A. The wide spread error in terms of %-biases in FIG. 4B made with a unified conversion $Slope_{composite}$ may produce a narrow band of error without additional calibrations by the connection function, as shown in FIG. 5B. Since a preset $Slope_{composite}$ is used to calculate the initial glucose concentration $G_{raw}$, the connection function makes the substantial error reduction for all data points regardless of the sensor responses without further calibration as long as the sensor responses are within the targeted response range. As shown in FIG. 4A, the upper boundary of the responses is almost three times that of the lower boundary of the response range.

Example embodiments provided herein describe use of a conversion function to determine an initial glucose concentration (e.g., based on a composite slope), and a connection function developed using multi-variate regression to determine a final glucose concentration from the initial glucose concentration. Alternatively, a single prediction equation may be developed using multi-variate regression without the use of separate conversion and connection functions. Example prediction equations are described in U.S. patent application Ser. No. 16/782,974, filed Feb. 5, 2020 and titled "APPARATUS AND METHODS OF PROBING SENSOR OPERATION AND/OR DETERMINING ANALYTE VALUES DURING CONTINUOUS ANALYTE SENSING," for example, which is hereby incorporated by reference herein in its entirety for all purposes.

In Table 1 below, the results of the initial conversion function, $G_{raw}$, and the results of the connection function, $G_{connect}$, are compared with results of a single prediction equation, $G_{predict}$, (such as a prediction equation as described in previously incorporated U.S. patent application Ser. No. 16/782,974). The following key advantages of the connection function by the PPM method can be seen from Table 1. For $G_{raw}$, the CGM signals (the primary data points) are converted to glucose values by a single $Slope_{composite}=0.1333$ for sensors with a wide range of responses that continue to vary over time. The results are wide spread with the individual glucose errors substantially deviated from the central behavior described by the composite $Slope_{composite}$ (MARD=23.4% and only 43.1% of the data being within ±20% error boundary). With the single prediction equation, the error spread is reduced by 50% and the MARD value is reduced by more than 60% to 7.79%, the data population approaching 91.3% within a ±20% error boundary. If the same data set is instead processed by a connection function after the conversion function with $Slope_{composite}=0.1333$, the error is further reduced from $G_{raw}$, even improved over $G_{predict}$, with the MARD reduced to 5.55% from 23.4% and the data population approaching 94.1% within ±15% and 98.1% within ±20% error boundaries respectively.

TABLE 1

Glucose calculation comparison for $G_{raw}$, $G_{predict}$, $G_{connect}$

| | | %-bias | %-MARD | ±15% | ±20% | n |
|---|---|---|---|---|---|---|
| $G_{raw}$ | Mean | −16.30 | 23.40 | 30.9 | 43.1 | 3294 |
| | SD | 21.20 | | | | |
| $G_{predict}$ | Mean | 0.61 | 7.79 | 86.6 | 91.3 | 3294 |
| | SD | 13.03 | | | | |
| $G_{connect}$ | Mean | −0.01 | 5.55 | 94.1 | 98.1 | 3294 |
| | SD | 7.68 | | | | |

Although both the single prediction equation and the connection function methods are derived by multivariate regression from the PPM parameters, targeting the relative error of $\Delta G/G_{raw}$ for regression in deriving the connection function reduces a larger portion of the error at the low glucose range than the single prediction equation approach. This can be seen in FIG. 6 for the comparison of the %-bias from the single prediction equation and the connection function where the open circles (○) denote the %-biases from $G_{predict}$ while the solid triangles (▲) denote the %-bases from $G_{connect}$. By virtue that the CGM sensors respond to the glucose concentrations in both the primary data points and the PPM currents, the connection function coupled with the composite conversion function, such as $(Iw-Ib)/Slope_{composite}$, provides glucose determinations with a narrow band of error. Thus, a broad scope connection is provided between in-vitro to in-vivo glucose testing.

Figure 7A:
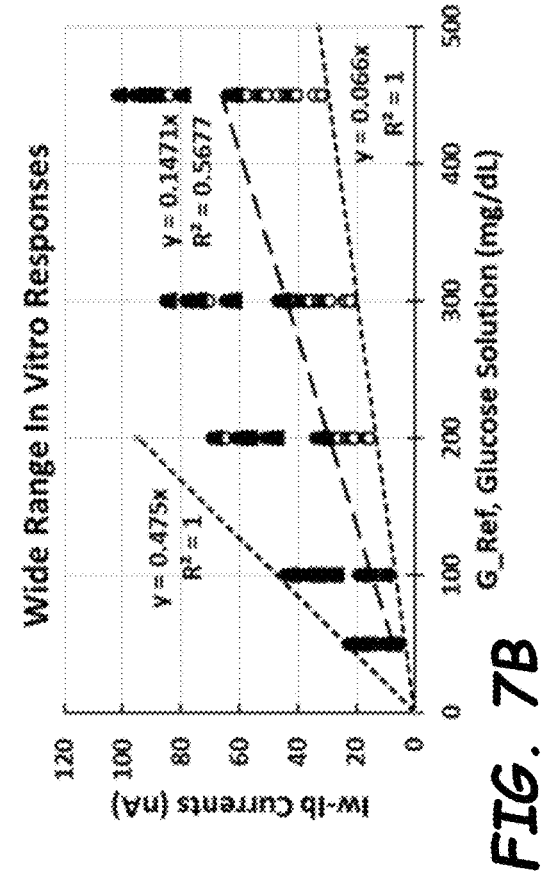
FIGS. 7A and 7B illustrate an example sensor response population, in accordance with embodiments provided herein.
Figure 7B:
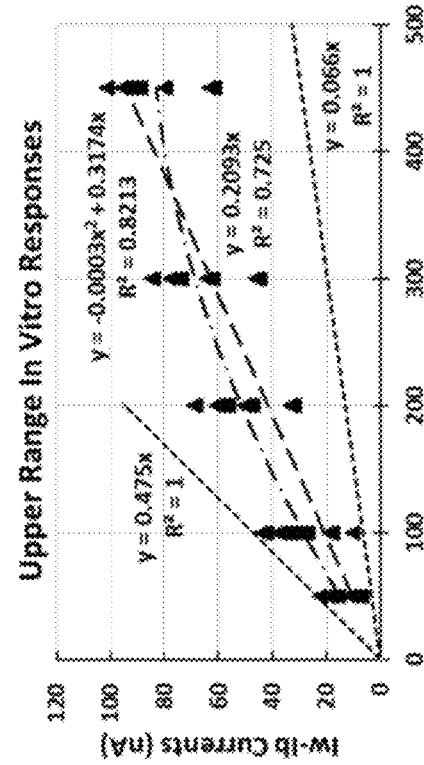

In the sensor manufacturing process, a wide range of sensor responses for the release specification may be encountered. FIGS. 7A and 7B illustrate an example sensor response population, in accordance with embodiments provided herein. The lower and upper boundaries are described approximately by two lines $y=0.066*x$ and $y=0.475*x$. For the entire response range, a simple linear line with $Slope_{composite}=0.1471$ characterizes the center of the in-vitro responses of the CGM sensors. The correlation coefficient $R^2=0.5677$ indicates only a moderate correlation between the signal (Iw-Ib) and the reference glucose value $G_{Ref}$ because of the wide range of sensor responses. There is a portion of the responses in the upper range and a portion of the responses in the lower range for the population (the dark triangles ▲ show responses in the upper range in FIG. 7B), as shown in FIGS. 7A and 7B. A single conversion function, as represented by the $Slope_{composite}$, may be used to convert the signals into $G_{raw}$ by $(Iw-Ib)/Slope_{composite}$. This is followed by a single connection function to reduce the raw %-bias values into a narrow band.

Figure 7C:
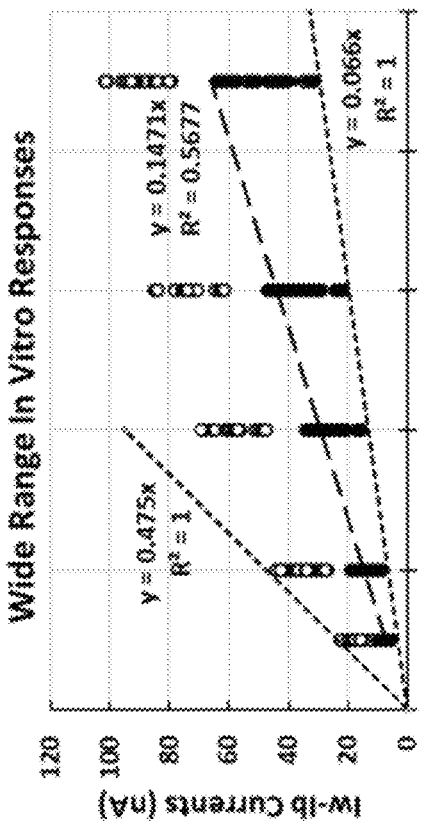
FIGS. 7C and 7D illustrate subdividing a wide range of sensor responses into two subsets of responses, an upper and a lower range, respectively, in accordance with embodiments provided herein.
Figure 7D:
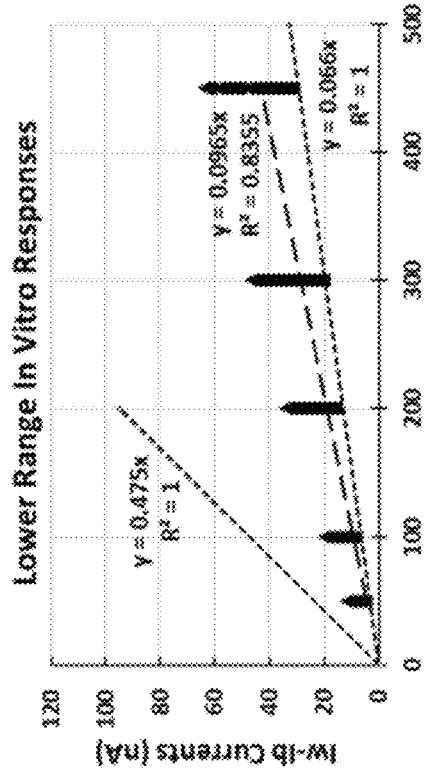
Figure 8B:
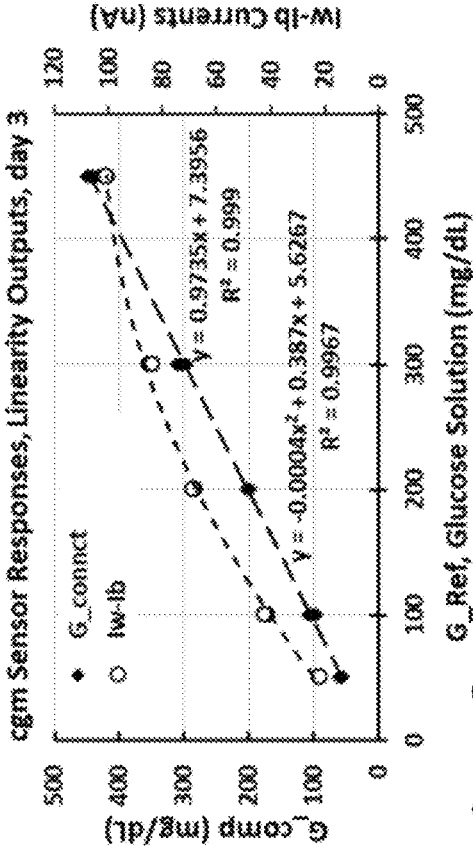
FIGS. 8A-8D illustrate output glucose concentration from a connection function with unity calibration versus reference glucose concentration on day 1, day 3, day 7, and day 14, respectively, in accordance with embodiments provided herein.
Figure 8D:
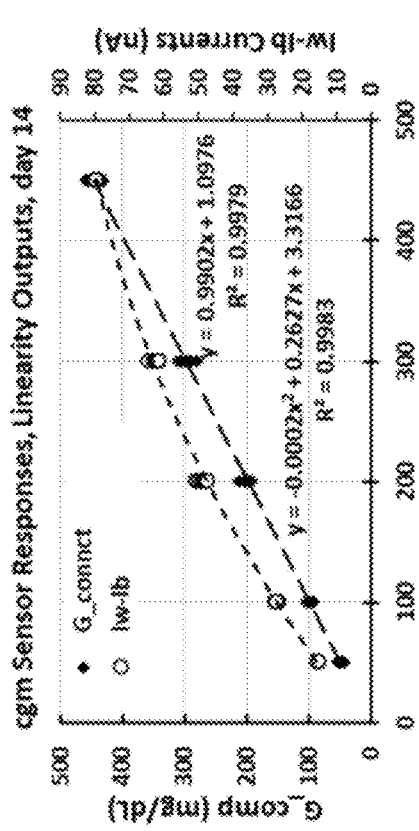
Figure 8A:
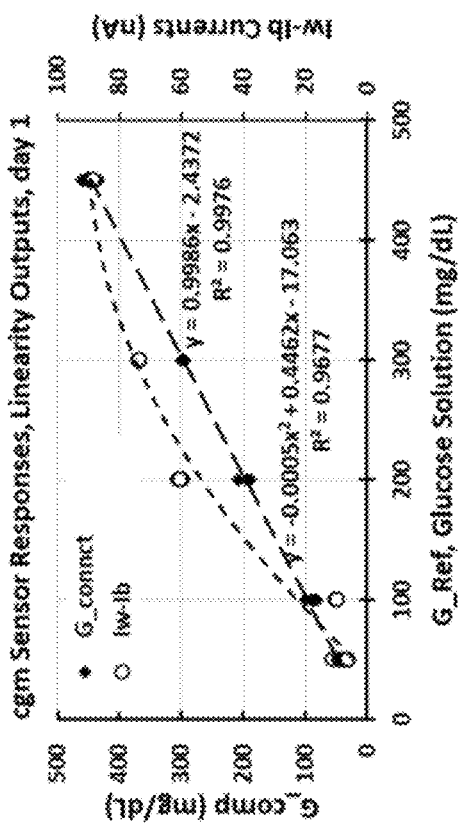
Figure 8C:
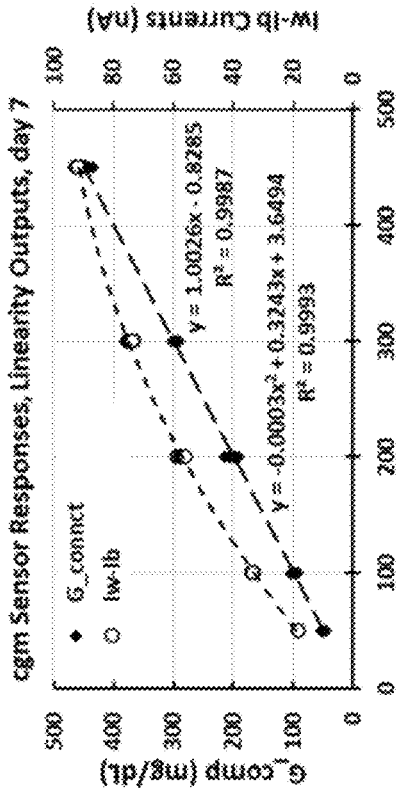

Given a wide response range for the CGM sensors, a prospective production response range may also be subdivided into more than one subset of responses. FIGS. 7C and 7D illustrate subdividing a wide range of sensor responses into two subsets of responses, an upper and a lower range, respectively, in accordance with embodiments provided herein. In FIGS. 7A-7D, the open circles (○) denote the entire range of responses (as shown in FIGS. 7A and 7B) while the solid triangles (▲) denote the subsets of either lower or upper response ranges (as shown in FIGS. 7C and 7D).

The content of FIG. 7C can be seen in FIG. 4A with an expanded y-axis where the lower and upper boundaries are approximately defined by two lines of 0.0667 to 0.1778 nA/mg/dL. For the lower subset of responses, the correlation coefficient for the linear regression of responses increases to 0.8355 from 0.5677 (the entire response population). For the upper subset of responses, the correlation coefficient for the linear regression of responses increases to 0.725 from 0.5677 (FIG. 7D). If a polynomial is used to describe the center response of the upper range, the correlation coefficient is further increased to 0.8213. Under this scenario, the conversion function is no longer the simple linear relationship with $Slope_{composite}$. However, the connection function linking the initial error by the initial conversion function of $\Delta G/G_{raw}$=f(PPM parameters) is still applied such that $G_{connect}$=$G_{raw}$/(1+connection function). In each case of the response subsets, the response function Signal=f(glucose) with an increased correlation coefficient helps to reduce the initial error $\Delta G/G_{raw}$. The connection functions further reduce the initial error to provide substantially better determinations of glucose concentrations for the CGM sensors than for one wide-ranging set of responses. The two connection functions are designed to have overlapping coverage for the marginal responses between the two subsets of responses. For each of the two subsets of responses, a broad scope connection is provided from in-vitro to in-vivo glucose where no further calibration is needed to produce glucose values in a narrow band of error. Thus, multiple conversion functions and/or multiple connection functions may be used.

Linearizing the glucose outputs from the non-linear signal responses is another advantage of the connection function. In the upper response region in FIG. 7B, the glucose response signals are intrinsically non-linear, which may be caused by an unbalanced enzyme-mediator condition of the biosensor. In biosensors where glucose oxidase (GO) is used as the enzyme, the mediator oxygen in and near the sensor surrounded by tissues may become limited, especially with sensors of very high response sensitivities. This may be considered as an unbalanced enzyme-mediator condition where the enzyme's oxidizing state cannot be regenerated fully and timely by the mediator, oxygen, at medium to high glucose concentrations. Subsequently, a non-linear response curve is obtained. A connection function can produce linearized glucose output values from the non-linear responses, in addition to accommodating a wide range of sensor responses in terms of sensor sensitivity variation. FIGS. 8A-8D show such conversion of non-linear responses to produce linear output glucose values for a CGM sensor where the open circles (○) denote the raw primary data points while the solid diamonds (♦) denote the output glucose values converted from the primary data points by a connection function. In so doing, the connection function not only accommodates different sensor sensitivities, but also accommodates non-linear responses at different times of the continuous in-vitro glucose sensing. These accommodations are so accomplished without further calibrations, as shown in day 1, day 3, day 7 and day 14 in FIGS. 8A-8D, respectively.

Figure 9B:
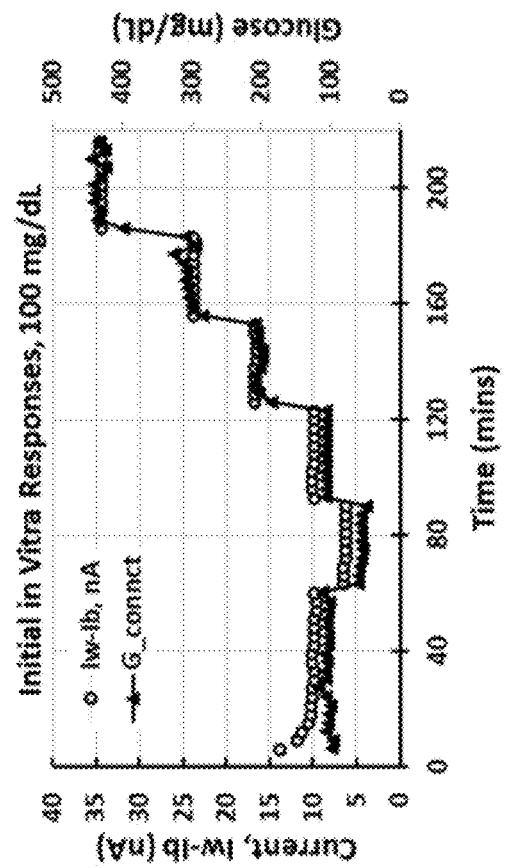
FIGS. 9A and 9B illustrate initial responses in linearity tests for a CGM sensor starting with 50 mg/dL and 100 mg/dL, respectively, as well as linear glucose outputs through use of a connection function with unity calibration, in accordance with embodiments provided herein.
Figure 9A:
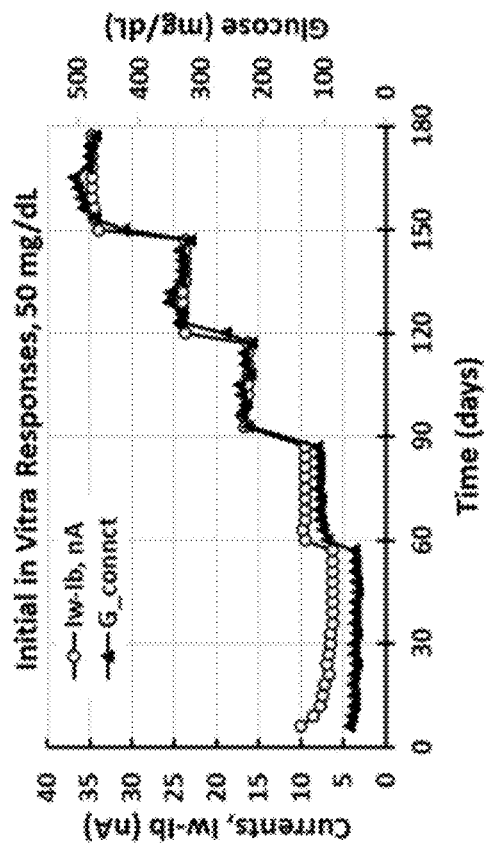

Operating in rapidly changing membrane conditions/environments and reporting accurate glucose values are yet other advantages offered by using a connection function, without requiring further calibrations. A rapidly changing membrane condition and/or environment is mostly reflected in the output signals changing over time. An example of such a condition is sensor response immediately after the sensor is submerged in an in-vitro test solution, as shown in FIG. 9A (with 50 mg/dL glucose solution) and FIG. 9B (with 100 mg/dL glucose solution), or sensor response immediately after the sensor is inserted into the skin subcutaneously. In both situations, in-vitro and in-vivo, the membrane of a sensor will undergo a rapid change of its structure, including the enzyme and the outer membrane, with respect to its initial dry state against the surrounding solvent molecules and/or tissues. For the examples in FIGS. 9A and 9B, this change is generally referred to as rehydration, and is most noticeable in the change of the initial responses as a decay in signals lasting 30-40 minutes, even at a constant glucose concentration. Such a subtle change during the rehydration process is also reflected in the PPM currents, which are incorporated in the regression of the connection function. A connection function derived from the PPM parameters can remove/minimize such decay effects during the initial state of continuous glucose sensing. The results can be seen in the glucose concentration plots of FIGS. 9A and 9B where the initial decay portions are virtually removed by applying the connection function to the current responses. This occurs without additional calibrations during continuous glucose sensing.

Figures 13A, 13B:
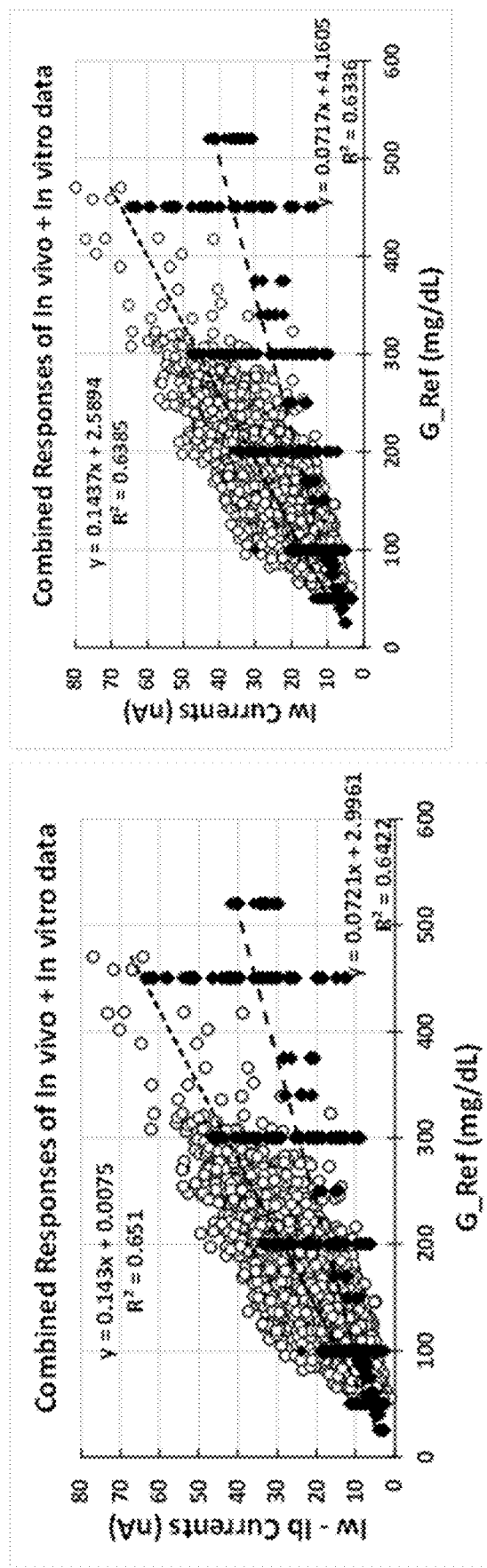
FIGS. 13A and 13B illustrate the combined responses of in-vivo and in-vitro data, with and without subtracting the currents Ib from the blank electrode, respectively, from a CGM clinical study and lab testing of multiple sensors, in accordance with embodiments provided herein.
Figures 13C, 13D:
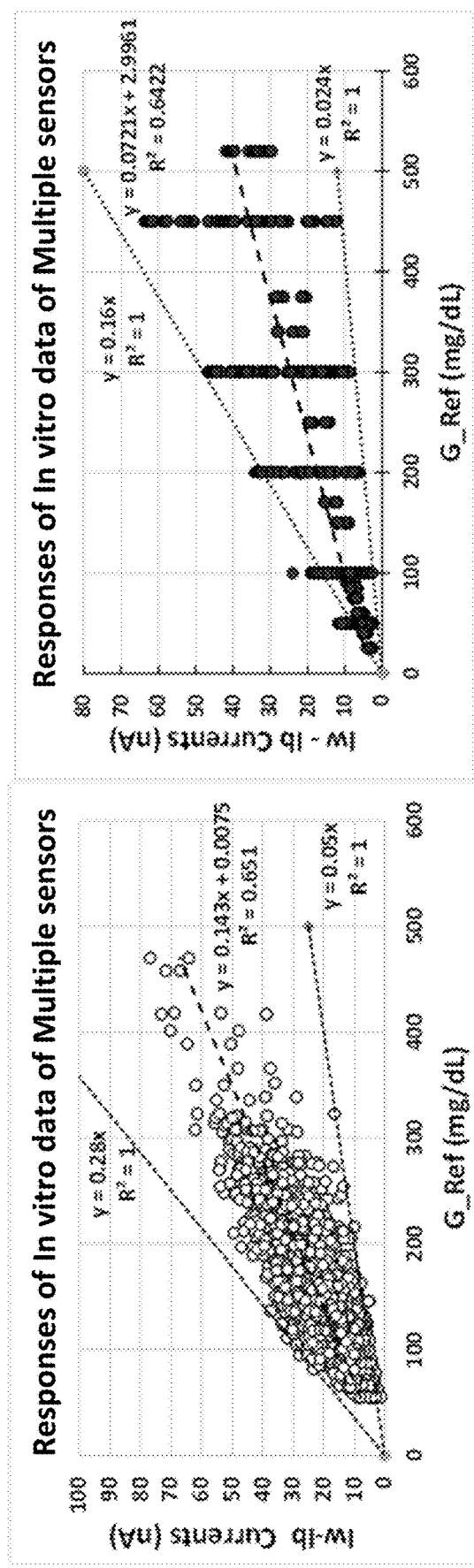
FIGS. 13C and 13D illustrate the responses of the in-vivo data and in-vitro data separately with their respective lower and upper boundaries from each study, in accordance with embodiments provided herein.

Yet another method of glucose determinations with reference to capillary glucose may be provided herein by a final adjustment function after making the broad scope connection (e.g., through use of a conversion function and connection function, as described). This adjustment may be implicitly implemented by combining the in-vitro and in-vivo data. Considering the discrete nature in in-vitro testing where only discrete levels of analyte concentrations are used, combining the data from in-vitro and in-vivo studies accommodates different sources of information embedded in data from different test settings. The goal is to provide accurate predictions of in-vivo analyte concentrations. Thus, in-vitro tests may be designed to provide different combinations and variations of sensors under different conditions, such as alternating the high and low oxygen conditions. FIGS. 13A and 13B provide examples of combining in-vitro and in-vivo data, with and without carrying out background subtraction for the working electrode currents, in accordance with embodiments provided herein. FIGS. 13C and 13D further separate the data sets from in-vivo and in-vitro tests, showing the variation ranges in sensitivity from different sensors and under different conditions, in accordance with embodiments provided herein. In this example, the in-vitro data was collected in a room temperature environment. Under this lower temperature condition, the responses are relatively lower compared to the responses of the in-vivo data (collected at ~32° C.). This temperature effect is compensated for with implicit implementation through the connection function derived from the regression process with data from different temperatures. This adjustment function may account for interstitial fluid lag even if the in-vitro to in-vivo connection is made without calibrations, employing relevant data from a clinical study, for example.

Table 2 below shows the results of data before (G-raw) and after (G-final) applying a connection function with adjustment to the combined data set of in-vitro data from multiple sensors and in-vivo data of 7-day CGM operations of multiple sensors. The unity calibration $slope_{composite}$ is 0.15385; that is, G-raw=(Iw−Ib)/0.15385, targeting the in-vivo data population. The mean %-bias for G-raw for the in-vivo data is slightly negative, but for the in-vitro data it is substantially negative. This large negative mean %-bias in part reflects the temperature effect for the in-vitro data collected at ~22-25° C. while the unity calibration slope is targeted at 32° C. under subcutaneous conditions. After compensation by the connection function with implicit adjustment, the mean %-bias values for the in-vivo, in-vitro, and the combined data are virtually zero. Furthermore, the %-MARD values are substantially reduced from the G-raw results. This shows the effectiveness of the unity calibration in conjunction with the connection function to overcome the varying sensitivity from different sensors, and their changes over time.

TABLE 2

Glucose calculation comparison for $G_{raw}$ and $G_{final}$

| | G-raw | | | G-final | | | |
|---|---|---|---|---|---|---|---|
| | %-bias | %-MARD | ±20% | %-bias | %-MARD | ±20% | n |
| In-vivo | −7.1 | 19.3 | 59.5 | −0.1 | 10.8 | 85.5 | 2998 |
| in-vitro | −36.7 | 39.2 | 20.1 | 0.3 | 7.1 | 95.3 | 2499 |
| All data | −20.5 | 28.1 | 41.6 | 0.1 | 9.1 | 90.0 | 5497 |

In summary, employing probing potential modulations (PPMs) as described herein provides enough self-sufficient information to accommodate sensitivity differences among different sensor lots, sensitivity change over an entire continuous monitoring time period, background variations due to different levels of interference species, and non-linear effects of glucose signals immediately after insertion and activation (providing a shortened warmup time). This may be accomplished with PPM currents and without factory and/or in-situ calibrations.

Figure 10:
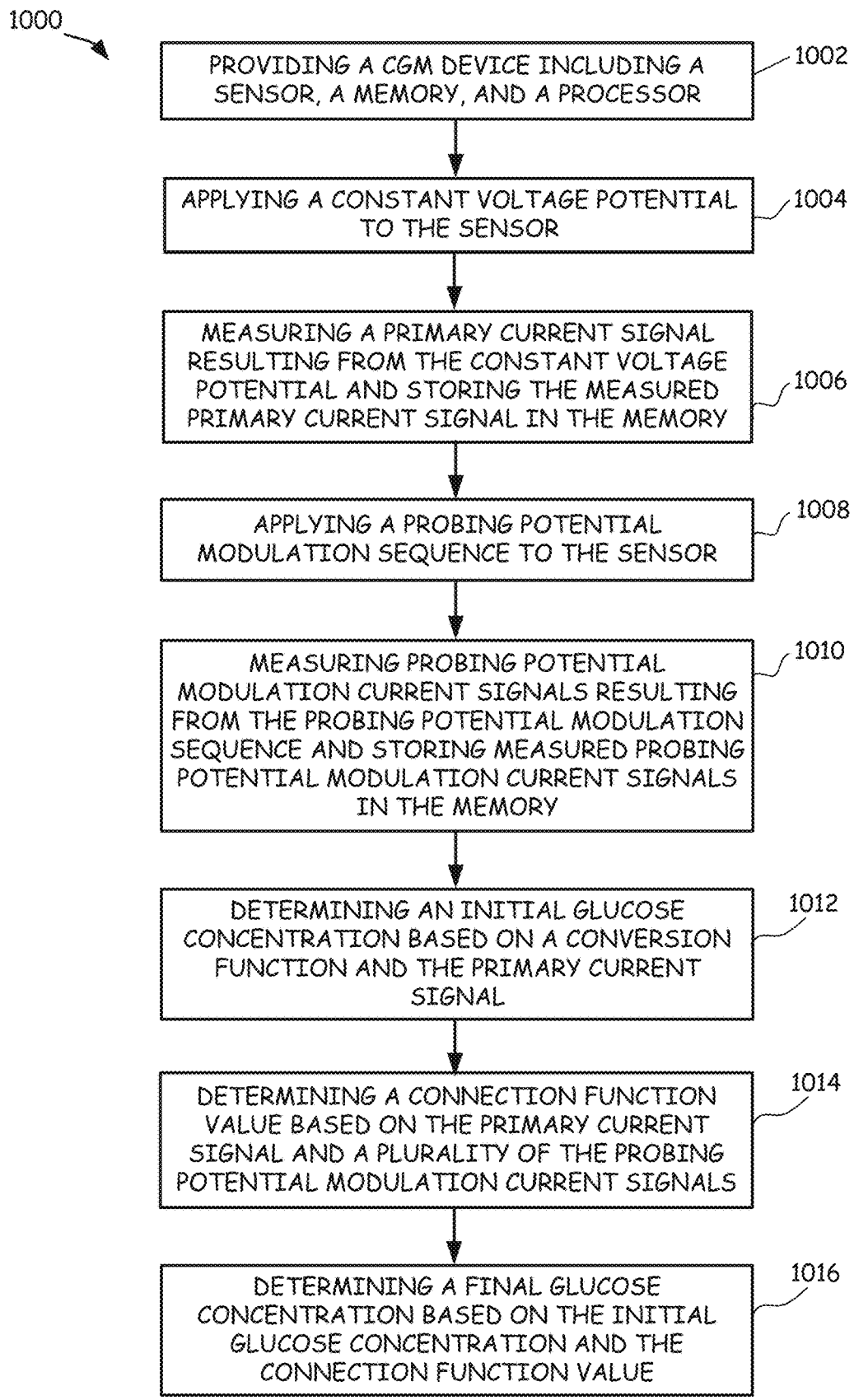
FIG. 10 illustrates an example method of determining glucose values during continuous glucose monitoring measurements, in accordance with embodiments provided herein.

FIG. 10 illustrates an example method 1000 of determining glucose values during continuous glucose monitoring measurements, in accordance with embodiments provided herein. With reference to FIG. 10, method 1000 includes, in Block 1002, providing a CGM device including a sensor, a memory, and a processor (e.g., CGM device 1100 or 1150 of FIGS. 11A-11B). In Block 1004, method 1000 includes applying a constant voltage potential to the sensor (e.g., $E_0$ in FIG. 3B). In Block 1006, method 1000 includes measuring a primary current signal resulting from the constant voltage potential and storing the measured primary current signal in the memory. In Block 1008, method 1000 includes applying a probing potential modulation sequence to the sensor (e.g., the PPM sequence of FIG. 3A). In Block 1010, method 1000 includes measuring probing potential modulation current signals resulting from the probing potential modulation sequence and storing measured probing potential modulation current signals in the memory. Method 1000 further includes: in Block 1012, determining an initial glucose concentration based on a conversion function and the primary current signal; in Block 1014, determining a connection function value based on the primary current signal and a plurality of the probing potential modulation current signals; and in Block 1016, determining a final glucose concentration based on the initial glucose concentration and the connection function value. The final glucose concentration may be communicated to a user (e.g., via display 1117 or 1122 of FIG. 11A or 11B).

In some embodiments, the PPM cycle or sequence is designed to take no more than half of the time of the primary data cycle (e.g., 3-5 minutes) to allow sufficient time for the constant voltage applied to the working electrode for the steady-state condition to resume before the next primary data point is recorded. In some embodiments, the PPM cycle may be on the order of about 1 to 90 seconds, or no more than 50% in a regular 180-second primary data cycle.

In one or more embodiments, the PPM cycle may be about 10-40 seconds and/or include more than one modulation potential step around the mediator's redox plateau. In some embodiments, the PPM sequence may be on the order of 10-20% of the regular primary data point cycle. For instance, when the regular primary data point cycle is 180 seconds (3 minutes), a PPM cycle of 36 second is 20% of the primary data point cycle. The remaining time of the primary data cycle allows the steady-state condition to resume at the constant applied voltage. For the potential steps in the PPM cycle, the durations are of a transient nature such that the boundary conditions of the measurable species created by these potential steps are non-steady-state. Thus, each potential step may be on the order of 1-15 seconds in some embodiments, about 3-10 seconds in other embodiments, and about 4-6 seconds in yet other embodiments.

In some embodiments, the probing potential modulation may step into the potential region of the non-diffusion-limited redox condition, or the kinetics region of the mediator (meaning the output currents are dependent on the applied voltage with the higher applied voltage producing higher output currents from the electrode). For instance, steps 2 and 3 of FIG. 3A are two potential steps in the kinetics region of the mediator generating the non-steady-state output currents from the electrode. On reversal of the potential steps, the same magnitudes of applied voltages (step 4 and step 5 of FIG. 3A) are resumed to probe the output currents of non-steady-state from the electrode.

Different embodiments of attending non-steady-state conditions may be employed. For instance, the non-steady-state conditions may also be probed by one-step directly to the target potential (step 2 in FIG. 3A) and returning to the starting potential (step 1 in FIG. 3A), which is followed by a second probing potential step going directly to a different potential (step 3 in FIG. 3A) in the kinetics region with a different non-steady-state condition, and then directly returning to the starting potential (step 1 or 6 in FIG. 3A). The intent is to modulate the applied potentials to create the alternation of steady-state and non-steady-state conditions for the measurable species at the electrode surface whereby signals from the non-steady-state may be used for determining the analyte concentrations.

Figure 11A:
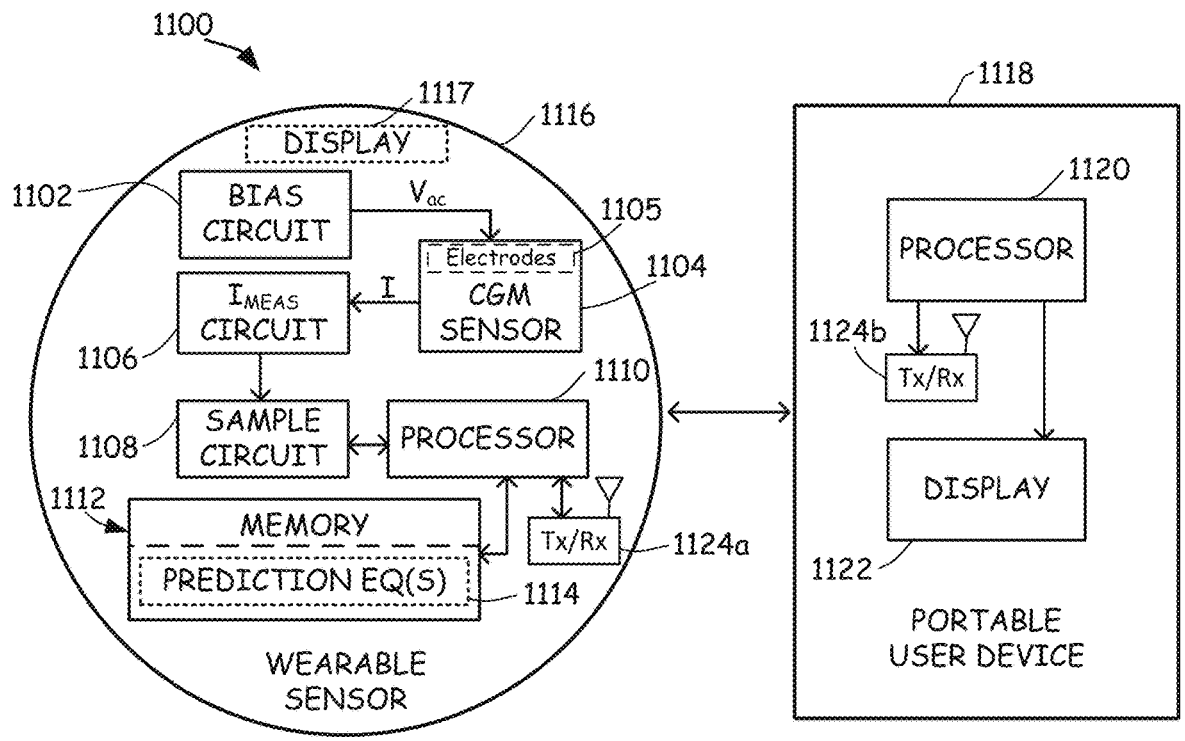
FIG. 11A illustrates a high-level block diagram of an example CGM device in accordance with embodiments provided herein.

FIG. 11A illustrates a high-level block diagram of an example CGM device 1100 in accordance with embodiments provided herein. Although not shown in FIG. 11A, it is to be understood that the various electronic components and/or circuits are configured to couple to a power supply, such as but not limited to a battery. CGM device 1100 includes a bias circuit 1102 that may be configured to couple to a CGM sensor 1104. Bias circuit 1102 may be configured to apply a bias voltage, such as a continuous DC bias, to an analyte-containing fluid through CGM sensor 1104. In this example embodiment, the analyte-containing fluid may be human interstitial fluid, and the bias voltage may be applied to one or more electrodes 1105 of CGM sensor 1104 (e.g., a working electrode, a background electrode, etc.).

Bias circuit 1102 also may be configured to apply a probing potential modulation sequence, as shown in FIG. 3A or another probing potential modulation sequence, to CGM sensor 1104. For example, probing potential modulation sequences may be applied for each primary data point as described above with reference to FIGS. 3A-3F. Probing potential modulation sequences may be applied before, after, or before and after measurement of a primary data point, for example.

In some embodiments, the CGM sensor 1104 may include two electrodes and the bias voltage and probing potential modulations (PPMs) may be applied across the pair of electrodes. In such cases, current may be measured through the CGM sensor 1104. In other embodiments, the CGM sensor 1104 may include three electrodes such as a working electrode, a counter electrode and a reference electrode. In such cases, the bias voltage and probing potential modulations may be applied between the working electrode and the reference electrode, and current may be measured through the working electrode, for example. The CGM sensor 1104 includes chemicals which react with a glucose-containing solution in a reduction-oxidation reaction, which affects the concentration of charge carriers and the time-dependent impedance of the CGM sensor 1104. Example chemicals include glucose oxidase, glucose dehydrogenase, or the like. In some embodiments, a mediator such as ferricyanide or ferrocene may be employed.

The continuous bias voltage generated and/or applied by bias circuit 1102 may range from about 0.1 to 1 volts versus the reference electrode, for example. Other bias voltages may be used. Example probing potential modulations values are described previously.

Probing potential modulation (PPM) currents and non-probing potential modulation (NPPM) currents through CGM sensor 1104 in an analyte-containing fluid responsive to probing potential modulations and a constant bias voltage may be conveyed from CGM sensor 1104 to a current measurement ($I_{meas}$) circuit 1106 (also referred to as current sensing circuitry). Current measurement circuit 1106 may be configured to sense and/or record current measurement signals that have magnitudes indicative of the magnitudes of the currents conveyed from CGM sensor 1104 (e.g., using a suitable current-to-voltage converter (CVC), for example). In some embodiments, current measurement circuit 1106 may include a resistor having a known nominal value and a known nominal precision (e.g., 0.1% to 5%, or even smaller than 0.1%, in some embodiments), through which the current conveyed from CGM sensor 1104 is passed. A voltage developed across the resistor of current measurement circuit 1106 represents the magnitude of the current, and may be referred to as the current measurement signal (or raw glucose signal $Signal_{Raw}$).

In some embodiments, a sample circuit 1108 may be coupled to current measurement circuit 1106, and may be configured to sample the current measurement signal, and may produce digitized time-domain sample data that is representative of the current measurement signal (e.g., digitized glucose signals). For example, sample circuit 1108 may be any suitable A/D converter circuit configured to receive the current measurement signal, which is an analog signal, and convert it to a digital signal having a desired number of bits as an output. The number of bits output by sample circuit 1108 may be sixteen in some embodiments, but more or fewer bits may be used in other embodiments. In some embodiments, sample circuit 1108 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio. Any suitable sampling circuitry may be employed.

Still referring to FIG. 11A, a processor 1110 may be coupled to sample circuit 1108, and may be further coupled to a memory 1112. In some embodiments, processor 1110 and sample circuit 1108 are configured to directly communicate with each other via a wired pathway (e.g., via a serial or parallel connection). In other embodiments, the coupling of processor 1110 and sample circuit 1108 may be by way of memory 1112. In this arrangement, sample circuit 1108 writes digital data to memory 1112, and processor 1110 reads the digital data from memory 1112.

Memory 1112 may have stored therein one or more equations 1114 (e.g., prediction equations such as a conversion function and a connection function, a single prediction equation, multiple conversion and/or connection functions, etc.), such as one or more connection functions, for use in determining glucose values based on primary data points (NPPM currents) and probing potential modulation (PPM) currents (from current measurement circuit 1106 and/or sample circuit 1108). For example, in some embodiments, two or more prediction equations may be stored in memory 1112, each for use with different segments (time periods) of CGM collected data. In some embodiments, memory 1112 may include a prediction equation (e.g., connection function) based on primary current signals generated by application of a constant voltage potential applied to a reference sensor, and a plurality of probing potential modulation current signals generated by application of a probing potential modulation sequence applied between primary current signal measurements.

Memory 1112 also may have stored therein a plurality of instructions. In various embodiments, processor 1110 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 1112 may include instructions that, when executed by the processor 1110, cause the processor 1110 to (a) cause the CGM device 1100 (via bias circuit 1102, CGM sensor 1104, current measurement circuit 1106 and/or sample circuit 1108) to measure current signals (e.g., primary current signals and probing potential modulation current signals) from interstitial fluid; (b) store current signals in memory 1112; (c) compute prediction equation (e.g., connection function) parameters such as ratios (and/or other relationships) of currents from different pulses, voltage steps or other voltage changes within a probing potential modulation sequence; (d) employ computed prediction equation (e.g., connection function) parameters to compute glucose values (e.g., concentrations) using prediction equations (e.g., conversion functions in combination with connection functions); and/or (e) communicate glucose values to a user.

Memory 1112 may be any suitable type of memory, such as but not limited to, one or more of a volatile memory and/or a non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 1112 may be packaged as a single chip or as multiple chips, for example. In some embodiments, memory 1112 may be embedded, with one or more other circuits, in an integrated circuit, such as, for example, an application specific integrated circuit (ASIC).

As noted above, memory 1112 may have a plurality of instructions stored therein that, when executed by processor 1110, cause processor 1110 to perform various actions specified by one or more of the stored plurality of instructions. Memory 1112 may further have portions reserved for one or more "scratchpad" storage regions that may be used for read or write operations by processor 1110 responsive to execution of one or more instructions of the plurality of instructions.

In the embodiment of FIG. 11A, bias circuit 1102, CGM sensor 1104, current measurement circuit 1106, sample circuit 1108, processor 1110, and memory 1112 including prediction equation(s) 1114, may be disposed within a wearable sensor portion 1116 of CGM device 1100. In some embodiments, wearable sensor portion 1116 may include a display 1117 for displaying information such as glucose concentration information (e.g., without use of external equipment). Display 1117 may be any suitable type of human-perceivable display, such as but not limited to, a liquid crystal display (LCD), a light-emitting diode (LED) display, or an organic light emitting diode (OLED) display.

Still referring to FIG. 11A, CGM device 1100 may further include a portable user device portion 1118. A processor 1120 and a display 1122 may be disposed within portable user device portion 1118. Display 1122 may be coupled to processor 1120. Processor 1120 may control the text or images shown by display 1122. Wearable sensor portion 1116, and portable user device portion 1118, may be communicatively coupled. In some embodiments, the communicative coupling of wearable sensor portion 1116 and portable user device portion 1118 may be by way of wireless communication via transmitter circuitry and/or receiver circuitry, such as transmit/receive circuit TxRx 1124a in wearable sensor portion 1116 and transmit/receive circuit TxRx 1124b in portable user device 1118, for example. Such wireless communication may be by any suitable means including but not limited to standards-based communications protocols such as the Bluetooth® communications protocol. In various embodiments, wireless communication between wearable sensor portion 1116 and portable user device portion 1118 may alternatively be by way of near-field communication (NFC), radio frequency (RF) communication, infra-red (IR) communication, or optical communication. In some embodiments, wearable sensor portion 1116 and portable user device portion 1118 may be connected by one or more wires.

Display 1122 may be any suitable type of human-perceivable display, such as but not limited to, a liquid crystal display (LCD), a light-emitting diode (LED) display, or an organic light emitting diode (OLED) display.

Figure 11B:
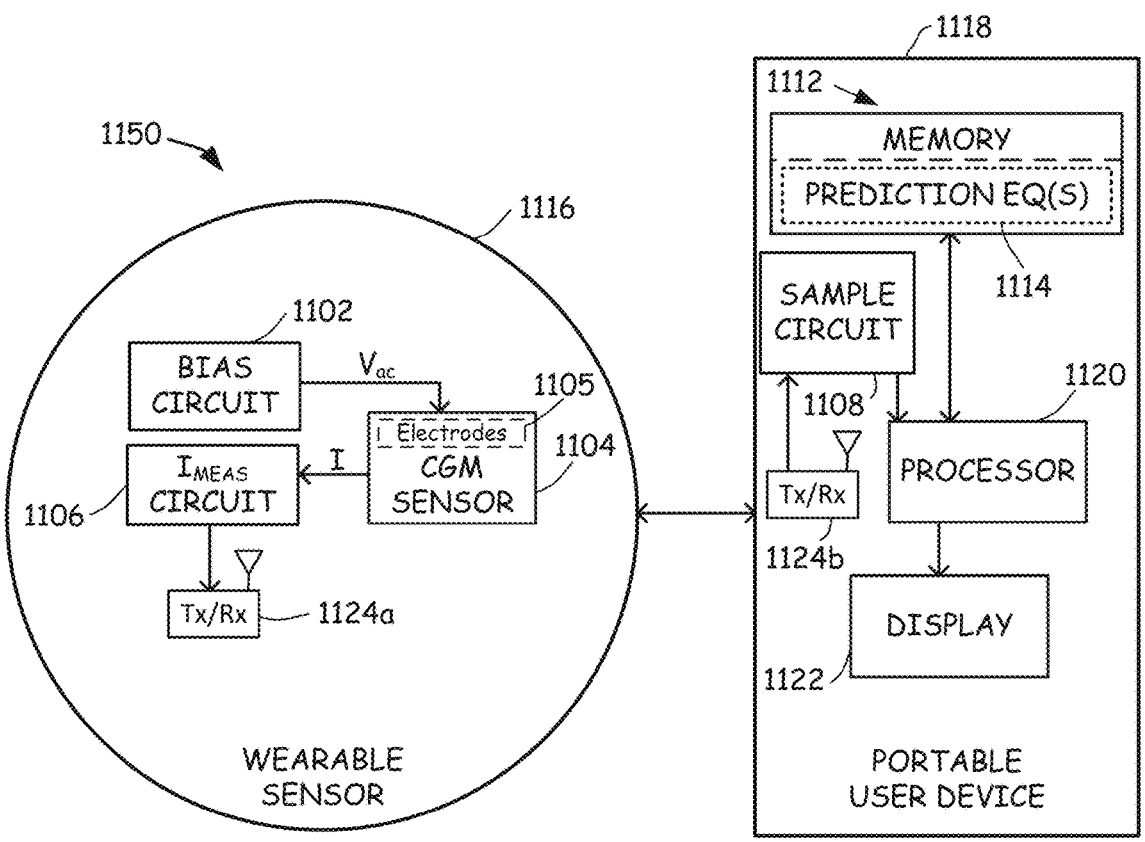
FIG. 11B illustrates a high-level block diagram of another example CGM device in accordance with embodiments provided herein.

Referring now to FIG. 11B, an example CGM device 1150 is shown that is similar to the embodiment illustrated in FIG. 11A, but having a different partitioning of components. In CGM device 1150, the wearable sensor portion 1116 includes the bias circuit 1102 coupled to the CGM sensor 1104, and the current measurement circuit 1106 coupled to the CGM sensor 1104. The portable user device portion 1118 of CGM device 1150 includes the sample circuit 1108 coupled to processor 1120, and the display 1122 coupled to processor 1120. Processor 1120 is further coupled to memory 1112 that may include prediction equation(s) 1114 stored therein. In some embodiments, processor 1120 in CGM device 1150 may also perform the previously-described functions performed by processor 1110 of CGM device 1100 of FIG. 11A, for example. Wearable sensor portion 1116 of CGM device 1150 may be smaller and lighter, and therefore less invasive, than CGM device 1100 of FIG. 11A because sample circuit 1108, processor 1110, memory 1112, etc., are not included therein. Other component configurations may be employed. For example, as a variation to the CGM device 1150 of FIG. 11B, sample circuit 1108 may remain on wearable sensor portion 1116 (such that portable user device 1118 receives digitized glucose signals from wearable sensor portion 1116).

Figure 12:
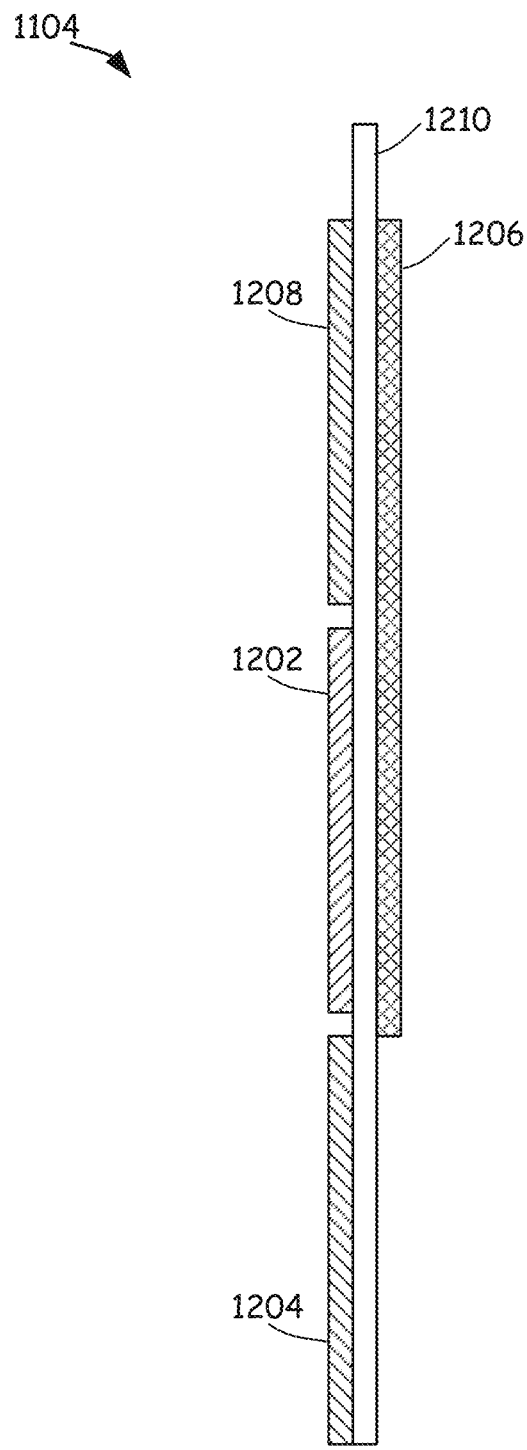
FIG. 12 is a side schematic view of an example glucose sensor in accordance with embodiments provided herein.

FIG. 12 is a side schematic view of an example glucose sensor 1104 in accordance with embodiments provided herein. In some embodiments, glucose sensor 1104 may include a working electrode 1202, a reference electrode 1204, a counter electrode 1206 and a background electrode 1208. The working electrode may include a conductive layer coated with a chemical which reacts with a glucose-containing solution in a reduction-oxidation reaction (which affects the concentration of charge carriers and the time-dependent impedance of the CGM sensor 1104). In some embodiments, the working electrode 1202 may be formed from platinum or surface roughened platinum. Other working electrode materials may be used. Example chemical catalysts (e.g., enzymes) for the working electrode 1202 include glucose oxidase, glucose dehydrogenase, or the like. The enzyme component may be immobilized onto the electrode surface by a cross-linking agent such as glutaraldehyde, for example. An outer membrane layer may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, reference electrode 1204 may be formed from Ag/AgCl. The counter electrode 1206 and/or the background electrode 1208 may be formed of a suitable conductor such as platinum, gold, palladium, or the like. Other materials may be used for the reference, counter and/or background electrodes. In some embodiments, the background electrode 1208 may be identical to the working electrode 1202, but without the chemical catalyst. Counter electrode 1206 may be isolated from the other electrodes by an isolation layer 1210 (e.g., polyimide or another suitable material).

While described primarily with regarding to glucose concentration determinations during continuous glucose monitoring, it will be understood that embodiments described herein may be used with other continuous analyte monitoring systems (e.g., cholesterol, lactate, uric acid, alcohol, or other analyte monitoring systems). For example, one or more prediction equations, such as one or more conversion and/or connection functions, may be developed for any analyte to be monitored through use of probing potential modulation output currents and their related cross terms.

The foregoing description discloses example embodiments of the disclosure. Modifications of the above-disclosed apparatus and methods which fall within the scope of the disclosure should be readily apparent to those of ordinary skill in the art. Accordingly, while the present disclosure has been disclosed in connection with example embodiments, it should be understood that other embodiments may fall within the scope of the disclosure, as defined by the following claims.

The invention claimed is:

1. A method of determining glucose values during continuous glucose monitoring (CGM) measurements for determining a sensor sensitivity of a sensor without in-situ calibrations, the method comprising:
providing a CGM device including the sensor, a memory, and a processor;
applying a constant voltage potential to the sensor;
measuring a primary current signal resulting from the constant voltage potential during a time period and storing information indicative of the primary current signal in the memory;
applying, during the time period, a probing potential modulation sequence to the sensor;
measuring a plurality of probing potential modulation current signals resulting from the probing potential modulation sequence and storing information indicative of the plurality of probing potential modulation current signals in the memory;
determining an initial glucose concentration value based on a conversion function and the information indicative of the primary current signal, the initial glucose concentration value having a percent bias relative to a reference glucose concentration value;
determining a connection function value for correcting the percent bias of the initial glucose concentration value, the connection function value based on the information indicative of the primary current signal for the time period, the information indicative of the plurality of probing potential modulation current signals for the time period, and the reference glucose concentration value;
determining the sensor sensitivity by comparing the information indicative of the plurality of probing potential modulation current signals for the time period, the information indicative of the primary current signal for the time period, and the connection function value to identify differences in the plurality of probing potential modulation current signals relative to the primary current signal;
determining a final glucose concentration value based on the initial glucose concentration value and the connection function value; and
adjusting the final glucose concentration value based upon the sensor sensitivity.

2. The method of claim 1, wherein applying the probing potential modulation sequence comprises applying a first voltage potential greater than the constant voltage potential, a second voltage potential less than the constant voltage potential, a third voltage potential less than the second voltage potential and a fourth voltage potential greater than the third voltage potential.

3. The method of claim 2, wherein determining the connection function value based on the plurality of probing potential modulation current signals comprises determining the connection function value based on ratios of the plurality of probing potential modulation current signals of different potential voltage steps within the probing potential modulation sequence.

4. The method of claim 3, wherein the probing potential modulation sequence includes 4 or more voltage steps.

5. The method of claim 1, wherein determining the connection function value based on the plurality of probing potential modulation current signals comprises determining the connection function value based on ratios of the plurality of probing potential modulation current signals.

6. The method of claim 1, wherein the primary current signal and the plurality of probing potential modulation current signals are working electrode current signals.

7. The method of claim 1, wherein the primary current signal is measured every 3 to 15 minutes.

8. The method of claim 1, wherein the conversion function comprises a slope determined based on in-vitro data from a plurality of sensors.

9. The method of claim 8, wherein the slope is determined based on in-vitro working electrode current versus reference glucose data.

10. The method of claim 9, wherein the in-vitro data is from the primary current signal.

11. The method of claim 1, wherein the connection function value is calculated based on the plurality of probing potential modulation current signals measured for a reference CGM sensor in response to the probing potential modulation sequence applied to the reference CGM sensor before or after the primary current signal is measured for the reference CGM sensor.

12. One or more non-transitory computer-readable media containing computer-executable instructions, that when executed by a processor perform a method of determining glucose values during continuous glucose monitoring (CGM) measurements for determining a sensor sensitivity of a sensor without in-situ calibrations, the method comprising:
applying a constant voltage potential to the sensor;
measuring a primary current signal resulting from the constant voltage potential during a time period and storing information indicative of the primary current signal;
applying, during the time period, a probing potential modulation sequence to the sensor;
measuring a plurality of probing potential modulation current signals resulting from the probing potential modulation sequence and storing information indicative of the plurality of probing potential modulation current signals;
determining an initial glucose concentration value based on a conversion function and the information indicative of the primary current signal;
determining the sensor sensitivity by comparing the information indicative of the plurality of probing potential modulation current signals for the time period and the information indicative of the primary current signal for the time period to identify differences in the plurality of probing potential modulation current signals relative to the primary current signal;
determining a final glucose concentration value based on the initial glucose concentration value; and
adjusting the final glucose concentration value based upon the sensor sensitivity.

13. The computer-readable media of claim 12, wherein applying the probing potential modulation sequence to the sensor comprises applying a first voltage potential greater than the constant voltage potential, a second voltage potential less than the constant voltage potential, a third voltage potential less than the second voltage potential and a fourth voltage potential greater than the third voltage potential.

14. The computer-readable media of claim 13, wherein the method further comprises:
determining a connection function value for correcting a percent bias of the initial glucose concentration value based on the information indicative of the primary current signal and the information indicative of the plurality of probing potential modulation current signals, wherein determining the final glucose concentration value is based, at least in part, on the connection function value.

15. The computer-readable media of claim 14, wherein the connection function value is based on ratios of the plurality of probing potential modulation current signals of different potential voltage steps within the probing potential modulation sequence.

16. The computer-readable media of claim 12, wherein the primary current signal and the plurality of probing potential modulation current signals are working electrode current signals.

17. The computer-readable media of claim 12,
wherein measuring the primary current signal comprises generating a digitized primary current signal from the primary current signal, and
wherein measuring the plurality of probing potential modulation current signals comprises generating a plurality of digitized probing potential modulation current signals from the plurality of probing potential modulation current signals.

18. The computer-readable media of claim 12, further comprising transmitting, to a portable user device, information indicative of the final glucose concentration value for presentation to a user of the portable user device.

19. The computer-readable media of claim 12, wherein the conversion function comprises a slope determined based on in-vitro data from a plurality of sensors.

20. The computer-readable media of claim 19, wherein the slope is determined based on in-vitro working electrode current versus reference glucose data.

21. The computer-readable media of claim 20, wherein the in-vitro data is from the primary current signal.

* * * * *